(12) United States Patent
Rossi et al.

(10) Patent No.: US 11,553,840 B2
(45) Date of Patent: Jan. 17, 2023

(54) ELECTRODE PLACEMENT AND TREATMENT SYSTEM AND METHOD OF USE THEREOF

(71) Applicant: RUSH UNIVERSITY MEDICAL CENTER, Chicago, IL (US)

(72) Inventors: Marvin A. Rossi, Oak Park, IL (US); Leopoldo Cendejas Zaragoza, Venustiano Carranza (MX)

(73) Assignee: RUSH UNIVERSITY MEDICAL CENTER, Chicago, IL (US)

( * ) Notice: Subject to any disclaimer, the term of this patent is extended or adjusted under 35 U.S.C. 154(b) by 895 days.

(21) Appl. No.: 15/532,642

(22) PCT Filed: Dec. 4, 2015

(86) PCT No.: PCT/US2015/063981
§ 371 (c)(1),
(2) Date: Jun. 2, 2017

(87) PCT Pub. No.: WO2016/090239
PCT Pub. Date: Jun. 9, 2016

(65) Prior Publication Data
US 2017/0360300 A1    Dec. 21, 2017

Related U.S. Application Data

(60) Provisional application No. 62/088,170, filed on Dec. 5, 2014.

(51) Int. Cl.
*A61B 5/00* (2006.01)
*A61B 5/055* (2006.01)
(Continued)

(52) U.S. Cl.
CPC ............ *A61B 5/0042* (2013.01); *A61B 5/055* (2013.01); *A61B 5/4094* (2013.01);
(Continued)

(58) Field of Classification Search
CPC ..... A61B 5/0042; A61B 5/055; A61B 5/4094; A61B 2034/104; A61B 2576/026; G16H 50/50; A61N 1/0529; G06F 19/3481
See application file for complete search history.

(56) References Cited

U.S. PATENT DOCUMENTS

2004/0122335 A1   6/2004  Sackellares et al.
2008/0064947 A1   3/2008  Heruth et al.
(Continued)

FOREIGN PATENT DOCUMENTS

WO    WO2011/034939    3/2011

OTHER PUBLICATIONS

Rossi et al. "Predicting white matter targets for direct neurostimulation therapy," Epilepsy Research, 2010. vol. 91, p. 176-186 (Year: 2010).*

(Continued)

*Primary Examiner* — Catherine B Kuhlman
*Assistant Examiner* — Sean A Frith
(74) *Attorney, Agent, or Firm* — Barnes & Thornburg LLP

(57) ABSTRACT

Certain aspects of the invention provide a system and a method for treating an epileptic condition or a tumor of the brain. In one embodiment, the method of treating the epileptic condition includes acquiring inter- and post-ictal imaging profiles and from the brain of the patient and determining an ictal propagation pathway based on the profiles. A volume of cortical activation is determined for each of a plurality of virtual electrode placement positions based on the ictal propagation pathway and the virtual electrode placement position. An electrode is implanted at a position selected from the plurality of virtual electrode placement positions, based on the volume of cortical activation at the implantation position. An electrical pulse is (Continued)

Depth Electrode Placement Planning System delivered from the electrode, where the electrical pulse is of a magnitude and duration effective to at least reduce the epileptic seizure.

21 Claims, 28 Drawing Sheets

(51) Int. Cl.
    *A61N 1/05*     (2006.01)
    *G16H 20/30*     (2018.01)
    *G16H 20/70*     (2018.01)
    *G16H 50/50*     (2018.01)
    *A61B 34/10*     (2016.01)

(52) U.S. Cl.
    CPC ........... *A61N 1/0529* (2013.01); *G16H 20/30* (2018.01); *G16H 20/70* (2018.01); *G16H 50/50* (2018.01); *A61B 2034/104* (2016.02); *A61B 2576/026* (2013.01)

(56) References Cited

U.S. PATENT DOCUMENTS

| | | | |
|---|---|---|---|
| 2009/0306532 A1* | 12/2009 | Tucker | A61B 5/055 600/544 |
| 2010/0286747 A1 | 11/2010 | Sabesan et al. | |
| 2012/0083701 A1 | 4/2012 | Osorio | |
| 2012/0116211 A1* | 5/2012 | McIntyre | A61N 1/36082 600/416 |
| 2012/0209344 A1* | 8/2012 | Rossi | A61N 1/362 607/22 |
| 2013/0060305 A1* | 3/2013 | Bokil | A61N 1/36146 607/62 |

OTHER PUBLICATIONS

Butson et al. "Patient-specific Analysis of the Volume of Tissue Activated During Deep Brian Stimulation," Neuroimage, 2007. vol. 34(2), p. 661-670 (Year: 2007).*

Potgieser et al. "The role of diffusion tensor imaging in brain tumor surgery: A review of the literature," Clinical Neurology and Neurosurgery, 2014. vol. 14, p. 51-58 (Year: 2014).*

International search report and written opinion for PCT/US2015/063981 dated Feb. 5, 2016, 7 pgs.

Poster for Development of a Depth Electrode Placement System for Direct Cortical Stimulation, Leopoldo Cendejas, Robert Dawe, Diego Garibay, Marvin A. Rossi, Rush University Medical Center, Chicago, IL, USA, Poster Session # 1.074 AES-2014, 1 pg.

Poster for Novel Depth Electrode Planning System for Direct Cortical Stimulation Therapy and Validation Using Subtracted Activated SPECT, Leopoldo Cendejas-Zaragoza; Marvin A. Rossi; Rush Epilepsy Center, Rush University Medical Center (RUMC), Chicago, IL, 2.078 AES-2015, 1 pg.

"Predicting white matter targets for direct neurostimulation therapy", Rossi et al., Epilepsy Research (2010) 91, 176-186.

"Prospective use of subtraction ictal SPECT coregistered to MRI (SISCOM) in presurgical evaluation of epilepsy", von Oertzen et al., Epilepsia, 52(12):2239-2248, 2011.

"Noninvasive Presurgical Estimation of Cortical Activation for Optimizing Intrcranial Electrode Placement for Responsive Neurostimulation in Refractory Epilepsy", Rossi et al., American Epilepsy Society 2005 Abstract, 1 pg.

"Preoperative Depth Lead Placement Planning to Activate Distant Cortex Replicates Visual Aura Semiology During Responsive Neurostimulation (RNS)", Rossi et al., American Epilepsy Society 2006 Abstract, 1 pg.

"Development of an Intracranial Lead Placement Planning System for Strategically Influencing the Epileptic Circuit", Rossi et al., American Epilepsy Society 2007 Abstract, 1 pg.

"Subtracted Activated Spect (SAS) Validates Propagation of Direct Neurostimulation Therapy in Double Band Heterotopia White Matter", Rossi et al., American Epilepsy Society 2009 Abstract, 1 pg.

"Comparing Isotropic and Anisotropic Brain Conductivity Modeling: Planning Optimal Depth-Electrode Placement in White Matter for Direct Stimulation Therapy in an Epileptic Circuit", Zargoza et al., Excerpt from the 2013 COMSOL conference in Boston, 13 pgs.

"Deep White Matter Track Record of Functional Integrity in Childhood Absence Epilepsy", Yang et al., Epilepsy Currents, vol. 12, No. 6 (Nov./ Dec. 2012 pp. 234-235.

Partial European Search Report for 15866110.8 dated Jun. 22, 2018, 16 pgs.

* cited by examiner

Figure 1 – Depth Electrode Placement Planning System

High Grade Glioma Cells and Injection of Carbon Nanotubes in an Induced E-Field

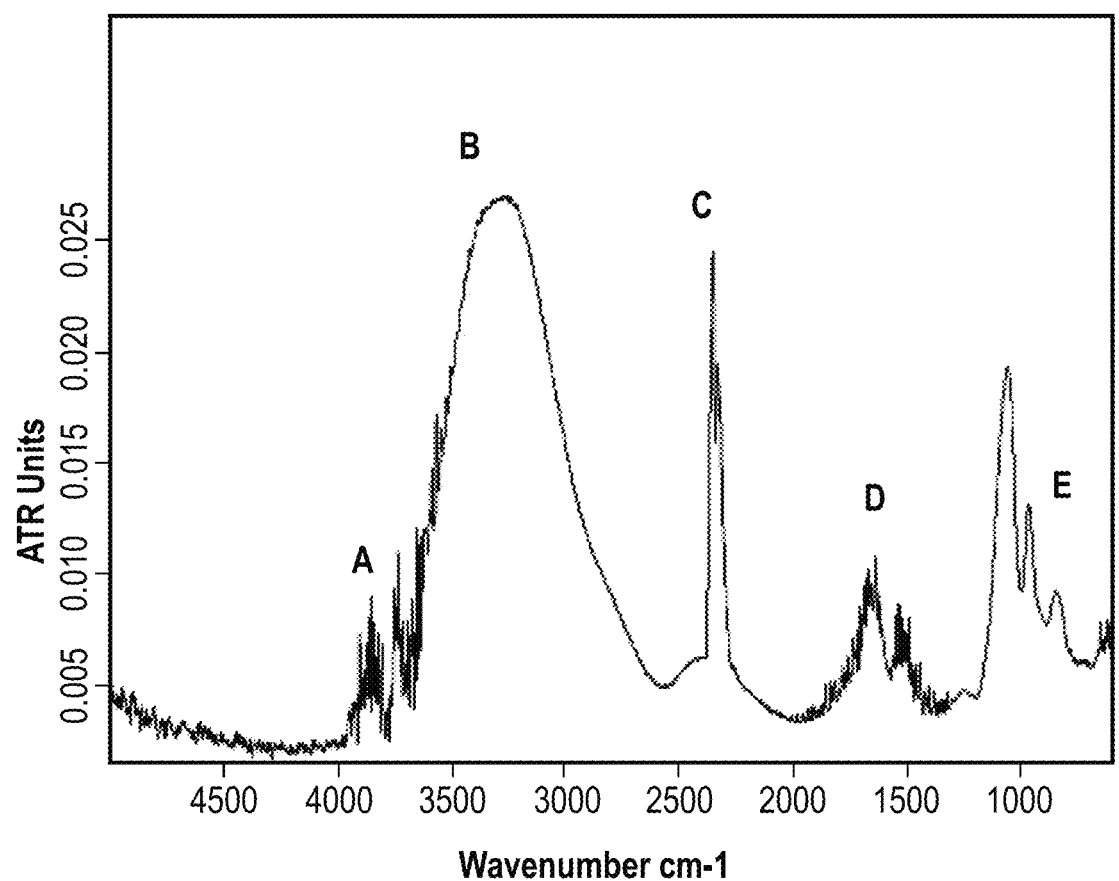
Figure 7(B)(ii)

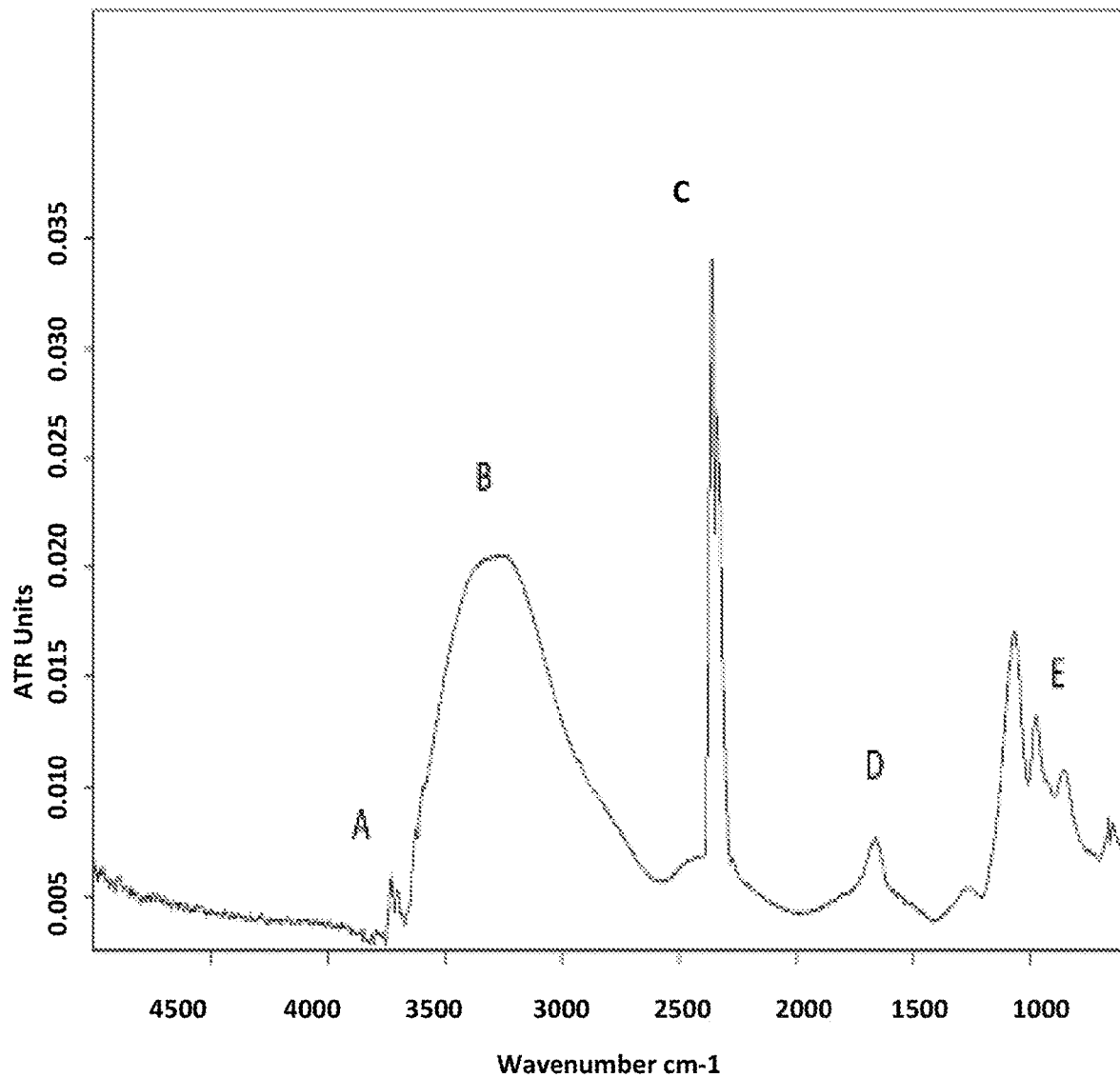
Figure 7(B)(iii)

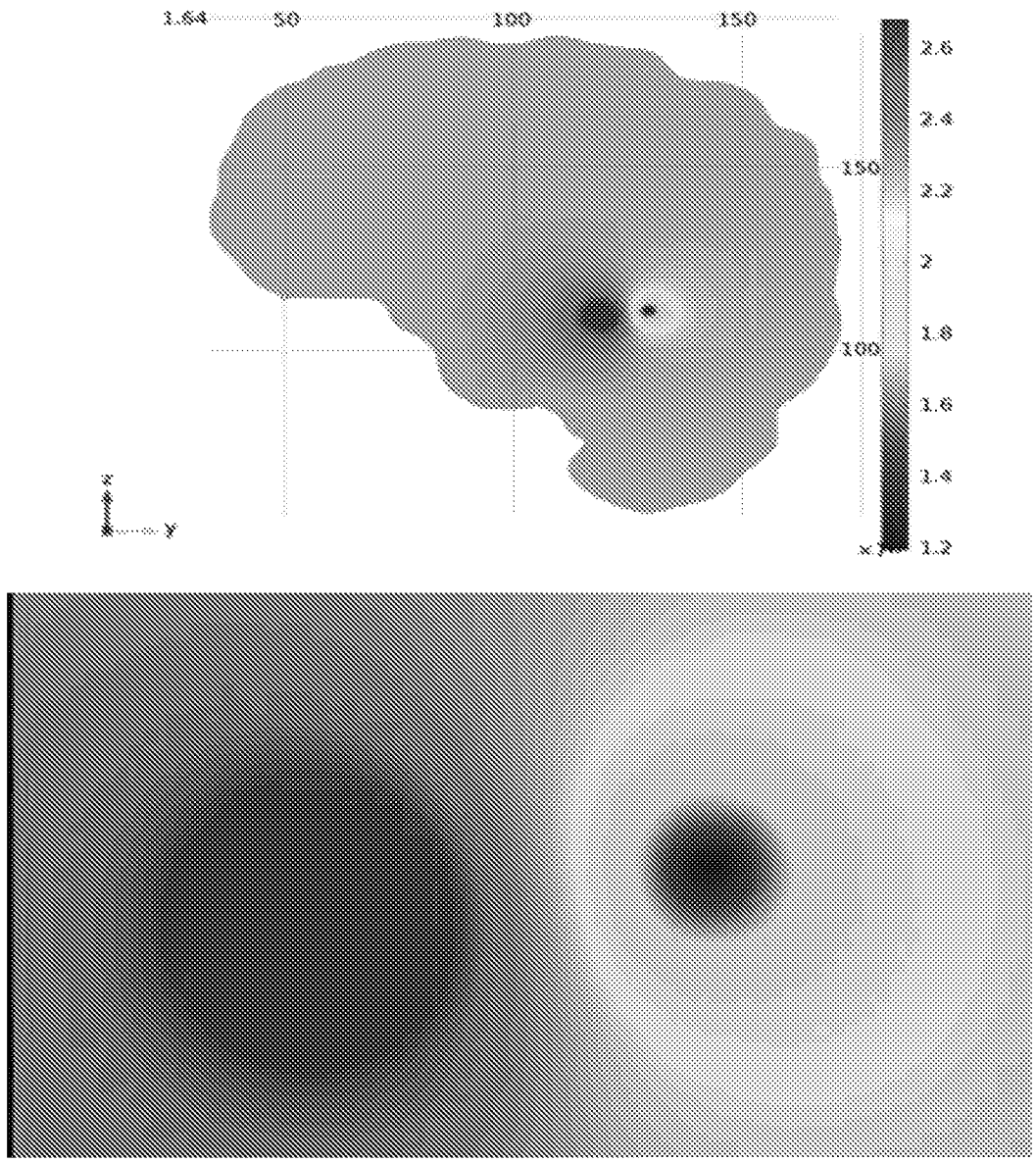
Figure 14(C)(ii)

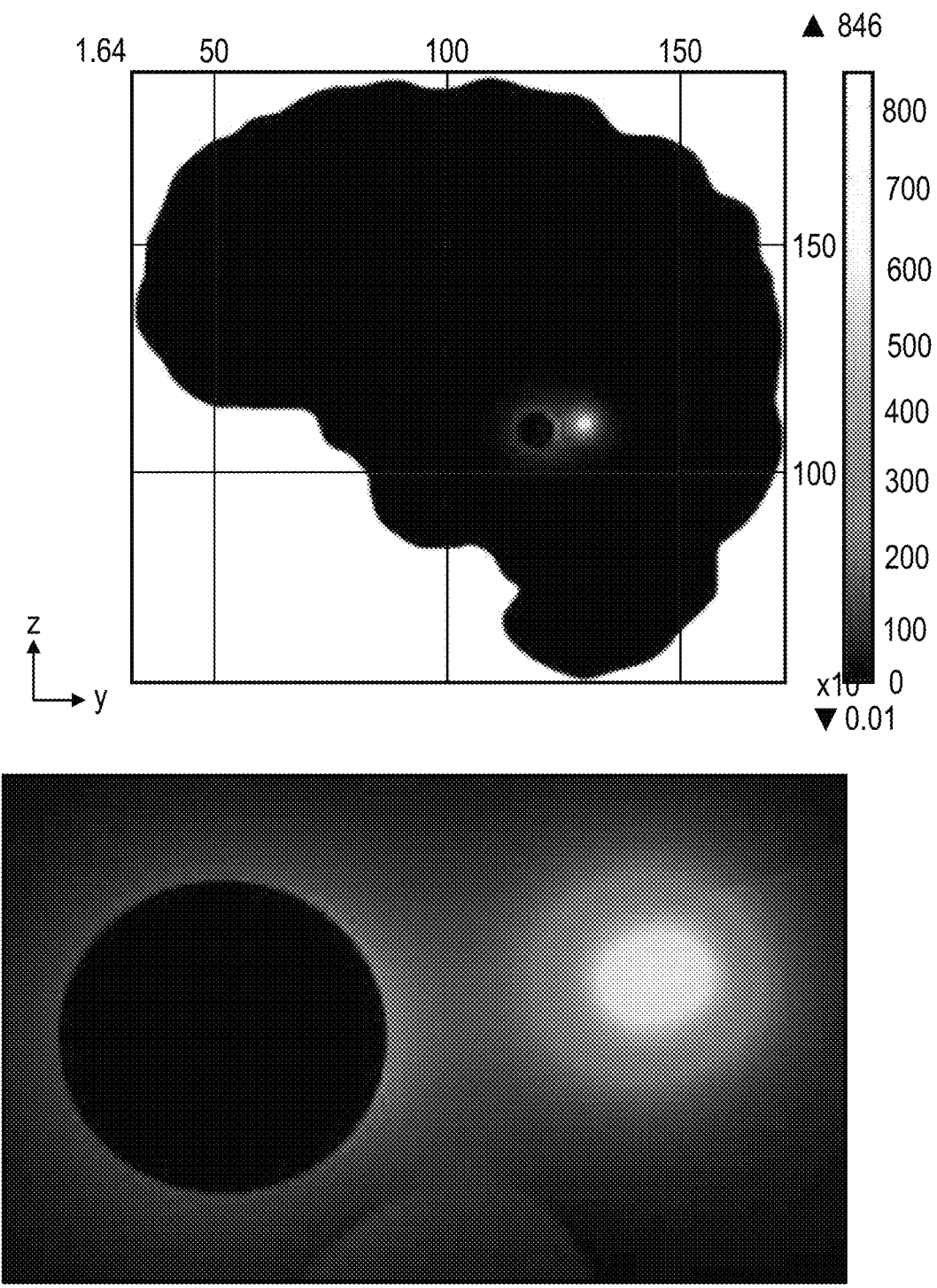
Figure 14(D)(ii)

ELECTRODE PLACEMENT AND TREATMENT SYSTEM AND METHOD OF USE THEREOF

This application is a National Stage of PCT/US2015/063981, filed Dec. 4, 2015, which claims the benefit of the filing date of U.S. Provisional Patent Application No. 62/088,170, filed Dec. 5, 2014, the contents of which applications are hereby incorporated by reference.

TECHNICAL FIELD

The present invention generally relates to a system and method for treating a tumor of the brain or an epileptic seizure condition. Certain embodiments of the method include determining an optimum position for the implantation of a depth electrode and/or a nano-transponder within the brain of a patient. When implanted, the electrode or transponder may be used to deliver an electrical charge of a magnitude effective in treating the tumor or epileptic seizure condition.

BACKGROUND

Epilepsy is one of the world's oldest recognized conditions. The World Health Organization (WHO) estimates that about 50 million people worldwide suffer from epilepsy. See WHO Fact Sheet No. 999 (January 2009). Epilepsy is caused by sudden, usually brief, electrical discharges in the brain. The symptoms can range from a brief loss of attention to prolonged and severe convulsions.

An EEG (electroencephalogram) remains the cornerstone for diagnosis of epileptic seizures. An EEG is a test that detects brain waves, or electrical activity in the brain. Sensitive electrodes are placed on the scalp to pick up electrical charges propagating through the brain. These charges are then mapped on a recording or a computer screen. The mapped electrical activity is interpreted to assist in the identification of the type and location of the seizure.

However, sometimes the root cause of epileptic seizures is difficult to find. When routine EEGs using electrodes on the scalp surface cannot locate where a patient's seizures are originating, neurosurgeons may need to do more invasive monitoring. Intracranial electrode placement is a surgical technique that puts electrodes directly on the surface of the brain, allowing for very precise and effective EEG monitoring. Intracranial EEG monitoring is used to precisely map epileptic areas of the brain. Not only does this technique allow for very precise mapping of areas causing the onset of seizures, but it also helps physicians identify and map critical areas of the brain, such as those controlling speech and motor control, that will need to be avoided during surgery.

In many patients with epilepsy, seizures can be well controlled with appropriate medication. However, current estimates indicate that 20-30% of patients with epilepsy are refractory to all forms of medical therapy. Many individuals are affected by such medically intractable epilepsy where surgical options are minimal or non-existent. In such cases, one alternative treatment method involves the use of a neuro-stimulator electrode implanted within the brain to deliver pulses of electrical stimulation when activity that could lead to a seizure is detected. The stimulation can help to prevent or reduce the effects of the seizure.

Such devices require the implantation of depth electrodes within the brain to allow for EEG monitoring of electrical activity inside the brain and for the delivery of the electrical pulses. Depth electrodes are probes that are inserted into specified areas of the brain via small holes made in the skull and covering of the brain. The insertion is typically stereotactically guided using, for example, magnetic resonance imaging (MRI) techniques, targeting a specific area within the brain. The entry point, trajectory and depth are calculated by a computer to allow for precise placement of the electrode.

Results emerging from the Food and Drug Administration (FDA) sponsored investigational neuro-stimulation trials are promising. However, nearly all patients enrolled in these studies continue to experience breakthrough seizures. Relatively bulky intracranial electrodes are utilized in these studies. The large size limits the number of electrodes that can be implanted. Limitations on the accuracy of placement of the electrodes may also result in limitations on the effectiveness of treatment.

Moreover, the implantation of a multiplicity of bulky electrode may result in brain tissue damage. Epileptic networks can be complex and may extend well beyond implanted bulky intracranial electrodes. To optimize stimulation of brain tissue, a multiplicity of nano-devices can be utilized, either alone or in combination with conventional in depth electrodes, to target specific brain cells while minimizing potential brain damage.

For example, carbon nanotube transponders that can be fabricated from a plurality of carbon nanotubes optionally attached to at least one biomolecule ligand and optionally connected to a nano-capacitor. An energy-releasing carbon nanotube transponder that can be placed in cellular tissue to treat multiple afflictions is disclosed in co-pending patent publication number PCT/US2010/048956, the contents of which are incorporation by reference.

In brain cancer, infiltrative primary high-grade neoplastic cells in the central nervous system (CNS) are often resistant to conventional chemotherapeutic and radiation therapies. Chemotherapy and radiation administered both inside the CNS and outside the blood brain barrier often cannot reach densely packed malignant cells even following resective debulking. Moreover, conventional chemotherapeutic agents can have limited efficacy due to factors ranging from systemic toxicity, to impaired drug transport secondary to decreased vascularization of the neoplasm core and P glycoprotein-mediated drug efflux. These limitations of conventional therapies have inspired investigational nanotechnology approaches to therapy.

SUMMARY OF THE PREFERRED EMBODIMENTS

In one aspect, the present invention provides a method for treating an epileptic seizure in the brain of a patient. In one embodiment, the method includes acquiring an inter-ictal imaging profile and a post-ictal imaging profile from the brain of the patient. These profiles are compared and an ictal propagation pathway determined on the basis of this comparison.

A plurality of virtual electrode placement positions for an electrode is determined based on the ictal propagation pathway and a volume of cortical activation determined for each virtual placement position based on the ictal propagation pathway and the virtual electrode placement position. An implantation position for the electrode is selected from the plurality of virtual electrode placement positions, based on the volume of cortical activation at the implantation position and the electrode implanted at this position. An electrical pulse, of a magnitude effective to at least reduce the epileptic seizure, is delivered from the electrode to cellular tissue within the volume of cortical activation.

In one embodiment the method also includes delivering a plurality of energy-releasing carbon nanotube transponders to a region of the brain of the patient and releasing an electric change from the plurality of energy-releasing carbon nanotube transponders. The energy-releasing carbon nanotube transponders are delivered to the cellular tissue at a position dependent upon the ictal propagation pathway.

In various embodiments, the energy-releasing carbon nanotube transponder includes at least one carbon nanotube having a nanocapacitor connecting to its first end. In one embodiment, the nanocapacitor is capable of storing a predetermined amount of electric energy and releasing the electrical energy in the form of a mean charge density in the range of between about $1.2 \times 10^{-5}$ and about $2.4 \times 10^{-5}$ Coulombs/cm$^2$. In yet another embodiment, the at least one carbon nanotube connects to the nanocapacitor and acts as a nanoswitch for releasing the predetermined amount of electrical energy to the cellular tissue in response to a change in the environment of the nanotube transponder. The plurality of the nanotube transponders is capable of releasing a biologically non-destructive electric charge in the range of between about 4 and about 20 microCoulombs/cm$^2$ to the cellular tissue.

In one embodiment, acquiring the inter-ictal imaging profile includes acquiring an inter-ictal diffusion tensor imaging MRI dataset and acquiring a post-ictal imaging profile includes acquiring a post-ictal diffusion tensor imaging MRI dataset. In another embodiment, determining the ictal propagation pathway includes determining fractional anisotropy in the inter-ictal diffusion tensor imaging MRI dataset and the post-ictal diffusion tensor imaging MRI dataset. Acquiring the inter-ictal and post-ictal imaging profiles may also include acquiring an inter-ictal and a post-ictal single-photon emission computed tomography dataset respectively. In one embodiment, determining a volume of cortical activation at each of the plurality of virtual electrode placement positions may include determining an activation function based on the electric potential produced by stimulation of the electrode in a homogeneous medium. In another embodiment, determining a volume of cortical activation at each of the plurality of virtual electrode placement positions may include determining an activation function based on the electric potential produced by stimulation of the electrode in an anisotropic medium.

In another embodiment, the method also includes acquiring a stimulation activated single-photon emission computed tomography dataset after delivery of the electrical pulse from the electrode, comparing this dataset with the volume of cortical activation at the implantation position, and validating the volume of cortical activation at the implantation position based on the comparison.

Another aspect of the invention provides a method for treating a tumor in the brain of a patient. One embodiment of the method includes acquiring a baseline diffusion tensor imaging MRI dataset from the brain of the patient and determining a tumor position based on this dataset. In this embodiment, a plurality of virtual electrode placement positions for an electrode is determined based on the tumor position and a volume of cortical activation determined at each of the placement positions.

An implantation position for the electrode is selected from the plurality of virtual electrode placement positions based on the volume of cortical activation at the implantation position and the electrode implanted at this position. An electrical pulse of a magnitude to effectively treat the tumor tissue is delivered from the electrode to tumor tissue within the volume of cortical activation. The method may also include delivering a plurality of energy-releasing carbon nanotube transponders as disclosed herein to a region of the brain of the patient and releasing an electric change from the transponders. The electric change from the plurality of energy-releasing carbon nanotube transponders pulse is of a magnitude to effectively treat the tumor tissue.

BRIEF DESCRIPTION OF THE DRAWINGS

In FIG. 9(A) the right hippocampal formation was injected with distilled PBS. In FIG. 9(B) the left hippocampal formation at the dentate gyrus was injected with 1 μL of 25 ng/mL 99% pure FITC-functionalized CNTs.

FIG. 10(D) shows a recording electrode composed of 0.005" 316L stainless steel.

FIG. 13(A) shows an agarose gel phantom imaged with a UV transilluminator.

FIG. 14(A) shows virtual electrodes were positioned within white matter that is adjacent to the hippocampal formation. FIG. 14(B) shows a spherical volume of modified conductivity following a Gaussian profile. FIG. 14(C) shows a FEM simulation comparing the baseline profile (14(C)(i)) to the CNT-M modified conductivity profile (14(C)(ii)). This comparison showed that the CNT-M modified model maintains a uniform electric potential within the area of increased conductivity. This equipotential behavior produces an electric field approaching zero within the area of higher conductivity; however, at the boundary a sharp increase in Electric Field is observed, see FIG. 14(D)(i) (baseline) and FIG. 14(D)(ii) CNT-M. This function served as the seed for generating modulated circuit tractography (MCT) mapping of the axon bundles which could potentially be activated via a depth lead, see FIG. 14(E).

FIG. 15(A) shows the analysis of the electric potential in a transept line is drawn through the volume of CNT-modified conductivity compared to a baseline profile (left peak) without CNT-Ms. FIG. 15 (B) shows parametric analysis of the E-Field in a transept line is shown through the volume of modified conductivity compared to a baseline profile without CNTs. FIG. 15(C) shows an expanded surface area provided by the volume of conductive CNT-Ms diminished the charge density to 1.63 μC/phase*cm$^{-2}$ when applying 5.12 μC/phase, which is below the damaging threshold.

DETAILED DESCRIPTION OF THE PREFERRED EMBODIMENTS

Definitions

Figure 1:
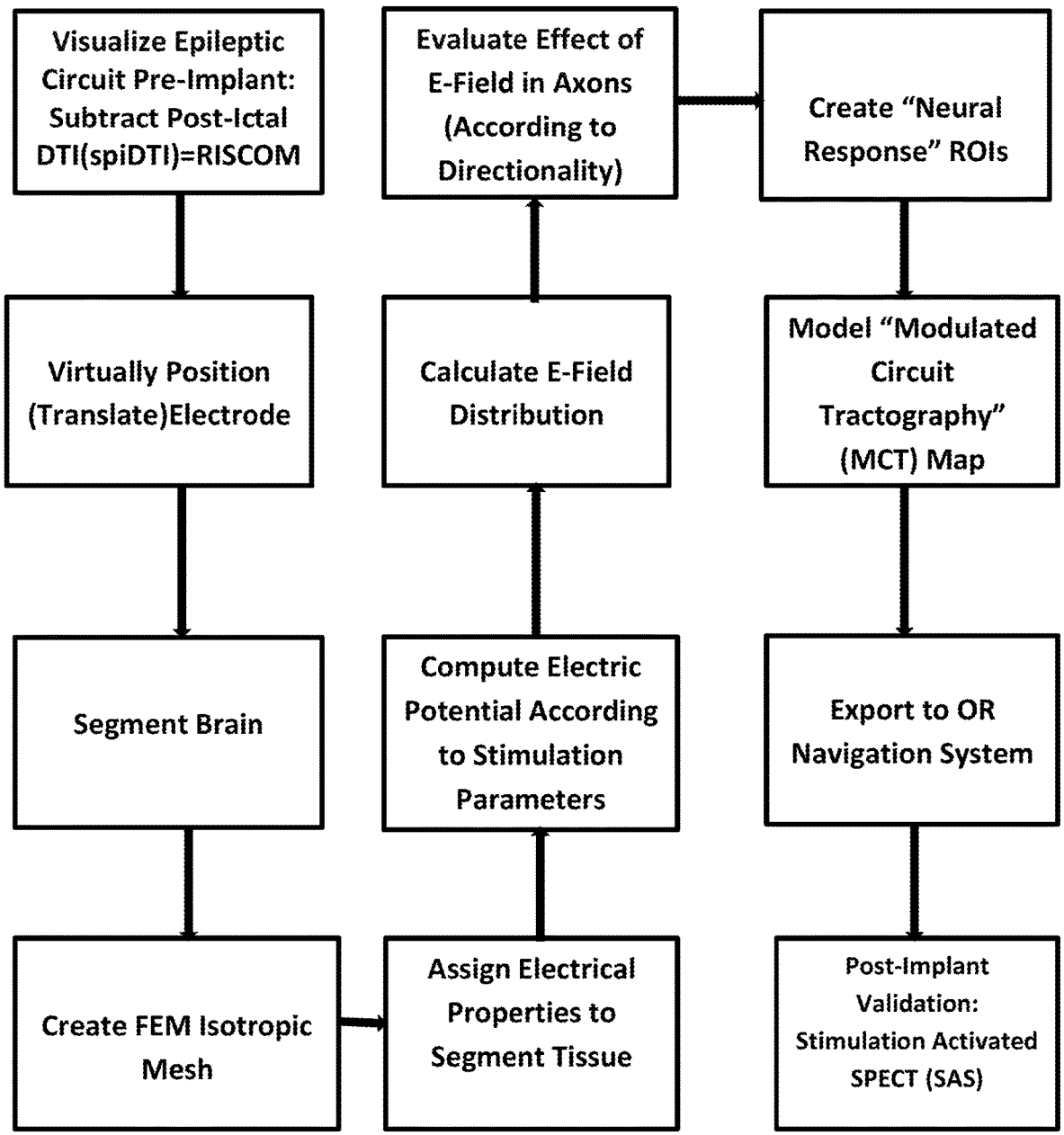
FIG. 1 is a flow diagram illustrating one embodiment of the steps in a depth electrode placement planning system.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

System and Methods for Treating a Disease or Condition of the Brain

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. In the discussions that follow, a number of potential features or selections of methods, methods of analysis, or other aspects, are disclosed. It is to be understood that each such disclosed feature or features can be combined with the generalized features discussed, to form a disclosed embodiment of the present invention.

Various aspects of the present invention provide an electrode placement planning method and system and also methods of using the method or system to treat a disease or condition of the brain of a human or a veterinary patient. In what follows, the system and method with be described with reference to a single depth electrode. However, if will be understood that the system and method are applicable to the placement of multiple depth electrodes within the brain of the patient. In general, at least two depth electrodes will be placed within the brain of the patient.

In one embodiment, the system and method provide for the propagation of an electrical current from the electrode to distant epileptic tissue during a direct neurostimulation therapy. In another embodiment, the system provides for the treatment of a pathological condition of the brain, for example, a cancer of the brain, by providing for the propagation of an electrical current from the electrode. The methods of the present invention may provide for the optimal placement of an electrode in the course of the treatment involving the delivery of an electrical current to the electrode to a region of the brain. In these embodiments, the electrical current may be sufficient to treat the epileptic condition or to kill a cancerous cell.

In certain embodiments, the method may also include the delivery and optimal placement of nano-electrodes, in the presence or absence of conjugated nano-capacitors. Examples of such nano-electrodes are disclosed in co-pending patent application publication number 2012-0209344, entitled "ENERGY-RELEASING CARBON NANOTUBE TRANSPONDER AND METHOD OF USING SAME" published Aug. 16, 2012, the contents of which are incorporated by reference.

The method may allow for the nano-electrodes to be delivered and optimally placed, for example by injection, to best implant sites, or one or more critical brain regions targeting pathological tissue, for example, brain tumor cells. In the case of epilepsy, such targeted brain tissue can be a critical node in an epileptic circuit. The delivery of the nano-electrodes can coat the brain surface and/or the nano-electrodes can be delivered into the brain parenchyma itself. The strategy can include bridging pathological tissue similar to lithography of electronic circuit boards. In certain embodiments, the nano-electrodes can be guided or steered through brain tissue by an electric field supplied from the implanted electrodes. Such an method as disclosed in co-pending PCT patent application number PCT/US2010/048956, the contents of which are incorporated by reference. Iron nanoparticles can be inserted into the carbon nanotubes to provide an ability to guide the complexes using an external magnetic field guidance system. The accuracy of such steering may be optimized by the use of the placement planning system disclosed herein.

Injecting the carbon nanotubes containing iron nanoparticles can provide the capability of guiding the complexes through a porous medium and offers the potential of guiding such complexes in living brain using an external magnetic field. Electrode placement may be modelled in vitro using agarose gel and hybrid microfluidic depth microelectrode arrays, for example those available from NeuroNexus, Ann Arbor, Mich., used to apply an optimal magnetic field strength to steer magnetic nanoparticle-carbon nanotube complexes in vivo. Such an ability augments the versatility of the nanocapacitor-carbon nanotube complexes for shaping the volume of cortical activation post-implantation of conventional depth electrodes housing the reservoir from which the nanocapacitor-carbon nanotube complexes can be injected into the medium. These complexes can also be conjugated or linked with fluorescent labels (e.g., FITC tagging), and therapeutic drug molecules such as growth factors. In particular, brain derived neurotrophic growth factor (BDNF) for influencing neural plasticity related changes surrounding the complexes.

The nano-electrodes may enhance the effectiveness of the treatment by increasing the effective range of the electric field generated by the depth electrodes during the treatment. In one embodiment, the effective range of the electric field around the depth electrode, and the nano-electrodes then these are present, is quantified by determining a volume of cortical activation ("VOCA") around the implanted electrodes.

One embodiment of the placement method utilizes intracranial depth electrodes for generating electric fields and for both steering the nano-devices strategically through brain, as well as providing therapy to pathological tissue (e.g., tumor cells, and/or epileptic networks). Such therapy may provide for the abatement the tissue of interest or for modulation of the epileptic circuit, respectively. That is, in the case of a hyper-excitable epileptic circuit, reverting the circuit to a non-pathological stable firing state.

When treating an epileptic condition, one goal of the placement method is the pre-implantation prediction of optimal electrode placement in cortical white matter for influencing the maximal extent of the epileptic circuit in the presence or absence of nano-electrodes. The workflow of one embodiment of the placement method is illustrated in FIG. 1. This method may include three fundamental techniques to determine responsive neurostimulation electrode placement in a patient having a tumor or epileptogenic regions, for example, bilaterally independent temporal lobe epileptogenic regions.

The method may include pre-implantation finite element modeling to predict the VOCA around an electrode using an 'activation function'. Here, the VOCA is an estimate of the extent of the electric field influencing neural tissue surrounding adjacent active electrodes prior to implantation. The calculations may include anticipated stimulation parameters for the electrode, such as the charge delivered to the electrode. Typically, the VOCA will expend approximately 4 mm from an implanted depth electrode. However, the extent of the VOCA will vary dependent upon the local environment surrounding the depth electrode, for example, the extent and geometry of white matter, grey matter and cerebrospinal fluid. The extent of the VOCA may be extended when nano-electrodes implanted within the brain.

Secondly, propagation of electrical stimulation therapy can be simulated pre-implantation using the VOCA model positioned in diffusion tensor imaging ("DTI") scans obtained from the patient's brain. DTI is a magnetic resonance imaging (MRI) method allows the mapping of the diffusion process of molecules, mainly water, in biological tissues, in vivo and non-invasively. Generally, diffusion within such tissues is not free, but reflects interactions with, for example, macromolecules, fibers or membranes. Water molecule diffusion patterns can therefore reveal microscopic details about tissue architecture, either normal or in a diseased state. Such imaging data is determined post-ictally and interictal DTI and the two datasets compared. This technique is termed subtraction post-ictal DTI ("spiDTI").

In addition, ratio ictal single-photon emission computed tomography ("SPECT") co-registered to the patient's MRI ("RISCOM") may also be used to facilitate visualizing the active epileptic circuit to which depth electrodes must interface. This technique allows for the visualization of blood flow within the brain. This image is made by computing the ratio of the ictal to the baseline image at every point. Essentially, each voxel in the ictal image is divided by the corresponding voxel in the baseline blood flow image, when the baseline activity in that voxel is significant. The RISCOM voxel value may also include a weighting factor. For example, the weighting factor may be calculated as: Weighting Factor=(Ictal+Baseline voxel)/(Max(Ictal+Baseline).) SISCOM (Subtracted Ictal SPECT CO-registered to MRI) may also be used to facilitate visualizing the active epileptic circuit. Here, the baseline is subtracted from the ictal at every point.

Finally, validation of the predicted stimulated anatomical targets may be determined post-implantation using stimulation activated SPECT ("SAS"). For example, cortical responsive neurostimulator (RNS) (NeuroPace, Inc, Mountain View, Calif.) electrodes. Such depth electrode implantation is guided by the pre-implant neural circuit model for maximizing modulation of the maximal extent of an epileptic circuit. White matter pathways are targeted such that myelinated axons are utilized to propagate electrical current distant from the source of stimulation. This hypothesis is tested post-RNS implant with actual activation of associated white matter depth electrodes. RNS current is 'injected' while capturing transient blood flow changes using stimulation activated SPECT (SAS).

SAS acquisition and processing may be performed at 4-18 months post-implantation of RNS depth electrodes. Bipolar stimulation of depth contacts is performed simultaneously with peripheral intravenous administration of 99Tc-HMPAO or 99mTC-ECD. The injection of radiotracer occurs during delivery off 6-12 high frequency stimuli (100-200 Hz) at 0.5 Hz (stimulation intensity=4.5-6 mA, pulse width=160 microseconds, burst duration=100 msec). Delivery of stimulation current is performed without recording an after discharge (seizure). A baseline SPECT acquired 36-48 hours later is normalized, subtracted, and co-registered the patient's 3D SPGR MRI.

Concordant alterations in distant focal blood flow can be shown for patients implanted with NeuroPace RNS depth electrodes. These neuroanatomically distant focal regions of hypoperfusion are associated with repetitive stimulation of consecutive bipolar depth contacts in white matter. Focal hypoperfusion throughout the epileptic circuit may indicate, among other possibilities, inhibition of cortical excitability downstream from stimulation. This information represents the maximal extent of cortical activation for a given set of stimulation parameters passed through a specific electrode contact geometry and orientation placed in human cortex. SAS can be used as a technique for validating presurgical mapping of the ictal onset zone. Presurgical planning using axonal pathways to direct the spread of current to an independent distant epileptic source can simplify the surgical approach with the available limited intracranial electrode set.

Pre-surgically, the modeling system may be used to predict white matter connectivity and side-effects to stimulation therapy. Post-implantation, SAS may validate focal blood flow changes in specific brain regions predicted pre-implant. The workflow demonstrates the feasibility of planning white matter-electrode placement with individual specificity to predict propagation of electrical current throughout a human epileptic circuit.

One application of the depth electrode planning system and method is to predict preoperatively the extent to which direct stimulation therapy applied, for example, using the RNS® Neurostimulator can propagate through pathological white matter during direct neurostimulation (RNS), including when amplified by nano-electrodes, for example carbon nanotube-based nano-electrodes. A pre-surgical model can be generated to calculate the VOCA in an electrode implant candidate. This model may include an iterative computationally-intensive process to test available stimulation parameters for bipolar depth electrodes. Such a model can include a method to calculate potential regions of hyperpolarization and depolarization with a VOCA and extent of neural activation amplified by nano-electrodes using an 'activation function.'

For example, an SPGR MRI sequence, interictal diffusion tensor imaging (DTI) dataset, and post-ictal DTI may be acquired for a specific patient. In one embodiment, DTI sequences are obtained on a 1.5 T—higher magnet strength MRI scanner using thin slices and diffusion measurements performed in at least 60 non-collinear directions. Six or more non-diffusion weights (b-values) may be used with a given repetition time. Ictal propagation pathways are determined using subtracted postictal diffusion tensor imaging (spiDTI) (See FIG. 1). This technique is performed by computing fractional anisotropy ("FA") in interictal and post-ictal sequences and subtracting the results. A given threshold is used to differentiate substantial changes in FA.

An iterative process for virtual electrode placement, and in some cases nano-electrode placement, may be modeled as follows: First, in a virtual model, depth electrodes are strategically positioned near the spiDTI signal, in a 3D segmented mesh generated according to the MRI scan. Second, the extracellular electric potential (EP) predicted by electric stimulation is calculated using the finite element method in a homogeneous isotropic medium or an anisotropic medium. In the isotropic model, the separate conductivity values were assigned to white matter, grey matter and cerebrospinal fluid. However, the conductivity was considered to be constant within each of the three categories.

In the anisotropic model, a separate conductivity is assigned for each voxel in the DTI dataset. Thus, the conductivity values may vary within each of the three categories. In certain embodiments, the conductively value is determined by calculating a conductivity matrix from the diffusion tensor matrix for each individual voxel in the DTI dataset. The voxel is positioned at its proper spatial coordinate and the conductivity value may be revised to consider the influence of any virtual nano-electrode positioned within the voxel. Hence, the anisotropic model may allow for account to be taken for the presence of lesions and the influence of micro- and nanodevices, for example, the nano-electrodes disclosed herein.

Third, the EP model is used to estimate an activation function for the cable equation of axons (E-field in axons—FIG. 1). In certain embodiments, this includes computing the second directional derivative in the direction of white matter tracts. This directionality is obtained from tensor fitting acquired from the post-ictal DTI. Fourth, the magnitude of the activation function is used to determine areas of hyperpolarization and depolarization adjacent to the electrodes. Fifth, generated depolarization/hyperpolarization regions of interest are used to identify influenced tracts in the patient-specific tractography model. In those embodiments including the use of nano-electrodes, aliquots of such particles, for example carbon nanotubes, may be steered through brain tissue and used to amplify conductivity of the native tissue conductivities.

Figure 5:
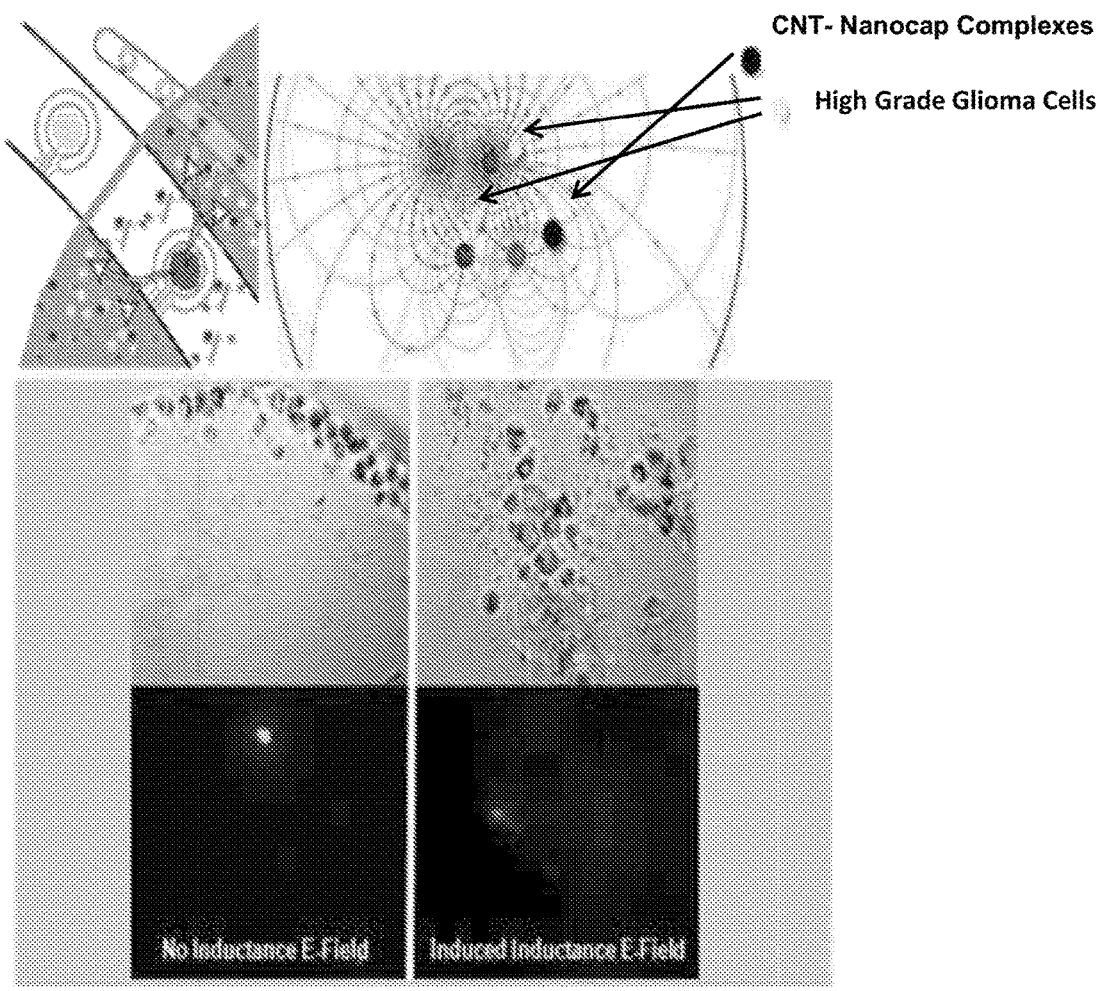
FIG. 5 is an illustration demonstrating the surrounding E-field magnitude amplification using single-walled carbon nanotubes (metallic and semi-conducting) between 50-200 nm in length. Cancer cells are shown destroyed in an E-field compared to E-field without carbon nanotube-based nanoelectrodes and no E-field.

The application of the activation function in the presurgical model may produce a VOCA defined as non-spherical overlapping regions of interest around the adjacent electrode where hyper-polarization and depolarization are determined. This data set demonstrates the ability to generate a preoperative electrode planning map for predicting 'best-implant' sites for both depth electrodes and nanoparticles along with steering and localization of carbon nano-electrode conductivity boosters (see FIG. 5 demonstrating nano-electrode proof-of-concept with high graded glioma cells). Furthermore, the application of the activation function is an improvement to previously reported activation regions produced by the magnitude of electric fields ((Rossi, et al. "Predicting white matter targets for direct neurostimulation therapy", Epilepsy Research 91, 176-186 (2010) as it considers not only the magnitude of the field but also its directionality effects in relation with the axon bundle orientation.

Figure 2:
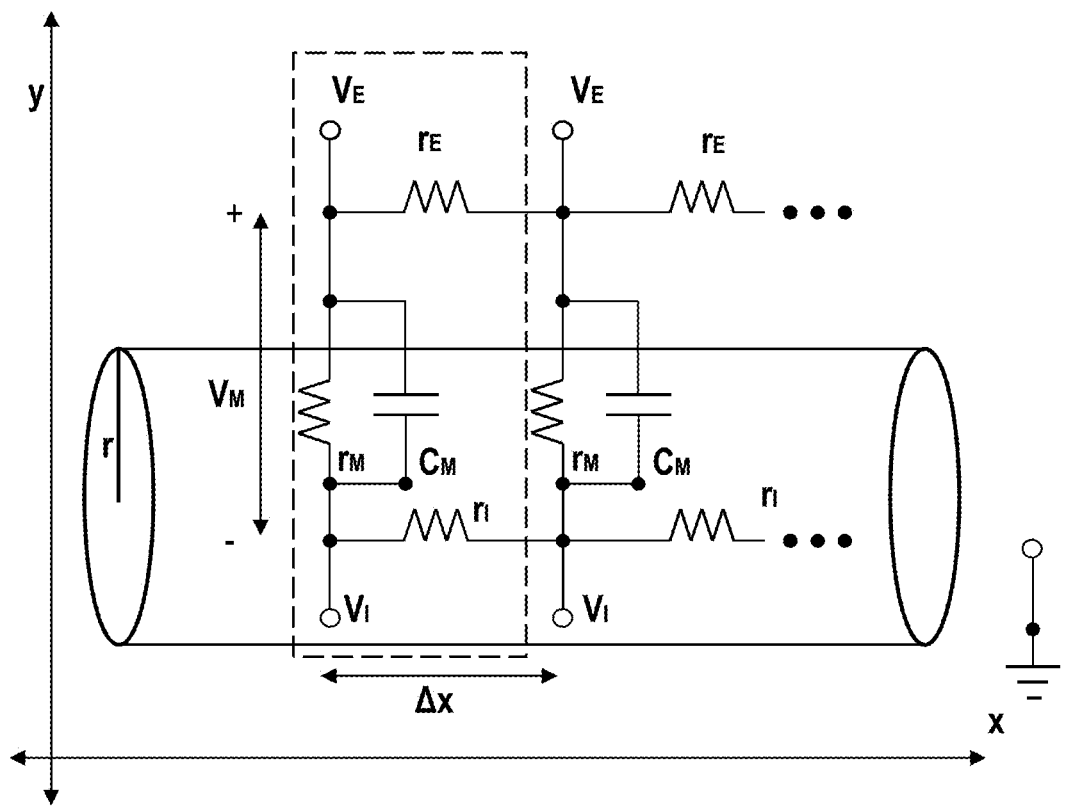
FIG. 2 is a schematic illustration of a lumped model for an axon oriented in the x direction is presented. Each compartment is considered to be composed by a membrane capacitance ($c_M$), connected in parallel with the membrane resistance ($r_M$). Compartments are connected to others through resistors in the extracellular ($r_E$) and intracellular space ($r_i$). The transmembrane voltage ($V_M$) is defined as the potential difference between the extracellular and intracellular fluid ($V_M = V_E - V_i$). In the figure, $\Delta x$ is the length of the compartment.

In one embodiment, the activation function is derived by analyzing a lumped element model of an axon compartment. In such a model, each compartment is composed by a membrane capacitance $c_M$, connected in parallel with the membrane resistance $r_M$. Compartments are connected to others through resistors in the extracellular $r_E$ and intracellular space $r_i$ (see FIG. 2). If geometric considerations are taken into consideration, then the values of $c_M$ and $r_M$ will change per unit area of membrane, whereas, $r_i$ changes per unit of cross-sectional area of the axoplasm. Thus, the values of $c_M$, $r_M$, and $r_i$ are converted into the specific membrane capacitance $C_M$ [μF/mm$^2$], specific membrane resistance $R_M$ [Ω/mm$^2$], and specific internal resistance $R_i$ (Ω·mm) respectively.

A non-homogenous partial differential equation (PDE) may be derived by applying Kirchoff's Current Law. This PDE is known as the cable equation (Equations 1, 2 and 3). The solution of this equation describes the transmembrane voltage ($V_M$) as a function of time. Note that the activation function is proportional to the second difference of the extracellular voltage ($V_E$). (Rattay, F., "Analysis of models for external stimulation of axons", IEEE Trans Biomed Eng, 10:974-7 (1986).)

$$\lambda^2 \frac{\Delta^2 V_M}{\Delta x^2} - \tau \frac{dV_M}{dt} - V_M = \lambda^2 \frac{\Delta^2 V_E}{\Delta x^2} \quad (1)$$

$$\lambda = \sqrt{\frac{rR_M}{2R_i}} \quad (2)$$

$$\tau = R_M C_M \quad (3)$$

In equation (1) λ is the length constant, which is directly proportional to the square root of the axon radius r and τ is the time constant for the membrane.

When the compartment length is very small (Δx→0) then equation (1) can be rewritten as equation (4):

$$\lambda^2 \frac{\partial^2 V_M}{\partial x^2} - \tau \frac{dV_M}{dt} - V_M = -\lambda^2 \frac{\partial^2 V_E}{\partial x^2} \quad (4)$$

In equation (4), the activation function is proportional to the second partial derivative of the extracellular potential with respect to the x direction $$\frac{\partial^2 V_E}{\partial x^2}.$$

In the model depicted in (FIG. 2), the axon is considered to be oriented in the x direction, thus the second difference $\Delta^2 V_E$ of extracellular potential is computed with respect to the x direction, $\Delta x^2$. However, axons can be in any spatial direction, therefore the second difference $\Delta^2 V_E$ should be computed with respect of the axon direction which can be described with normal vector n̂. Thus, the activation function is proportional to the second directional derivative of the extracellular potential $V_E$ in the axon direction within a Cartesian coordinate system, which can be calculated with the equations (5) and (6).

$$\text{first}(x,y,z) = \nabla V_E(x,y,z) \cdot \hat{n}(x,y,z) \quad (5)$$

$$\text{second}(x,y,z) = \nabla \text{first}(x,y,z) \cdot \hat{n}(x,y,z) \quad (6)$$

Where first(x,y,z) is the first directional derivative of the electric potential on the direction of axons, second(x,y,z) is the second derivative of the electric potential on the direction of axons $\nabla V_E(x,y,z)$ is the gradient of the extracellular electric potential, n̂(x,y,z) is a normal vector field that represents axon directionality, and $\nabla V_E(x,y,z) \cdot \hat{n}(x,y,z)$ is the scalar product between $\nabla V_E(x,y,z)$ and n̂(x,y,z). The negative gradient of the electric potential is the electric field $\vec{E}$, thus the second directional derivative depends on the magnitude and direction of $\vec{E}$, and the direction of the axon n̂. Equations (7) and (8) respectively.

$$\text{first}(x,y,z) = (-\vec{E}(x,y,z) \cdot \hat{n}(x,y,z)) \quad (7)$$

$$\text{second}(x,y,z) = (\nabla \text{first}(x,y,z) \cdot \hat{n}(x,y,z)) \quad (8)$$

Previous publications have determined that qualitative predictions of neural activation by extracellular sources can be evaluated by computing the second difference of the extracellular potential (Rattay, 1986). Regions of depolarization can be identified where the second difference is positive, while hyperpolarization regions can be identified where the second difference is negative (McIntyre et al., 2004). For the present embodiments, the second directional derivative may be used instead of the second difference.

Two steps were considered for computing the extracellular electric potential: The first step consisted in creating a patient specific Finite Element Model (FEM) where a CAD model of the depth electrode was placed. The second step consisted in solving a system of partial differential equations to obtain $V_E$ using the FEM model that was obtained in the first step.

Figure 3:
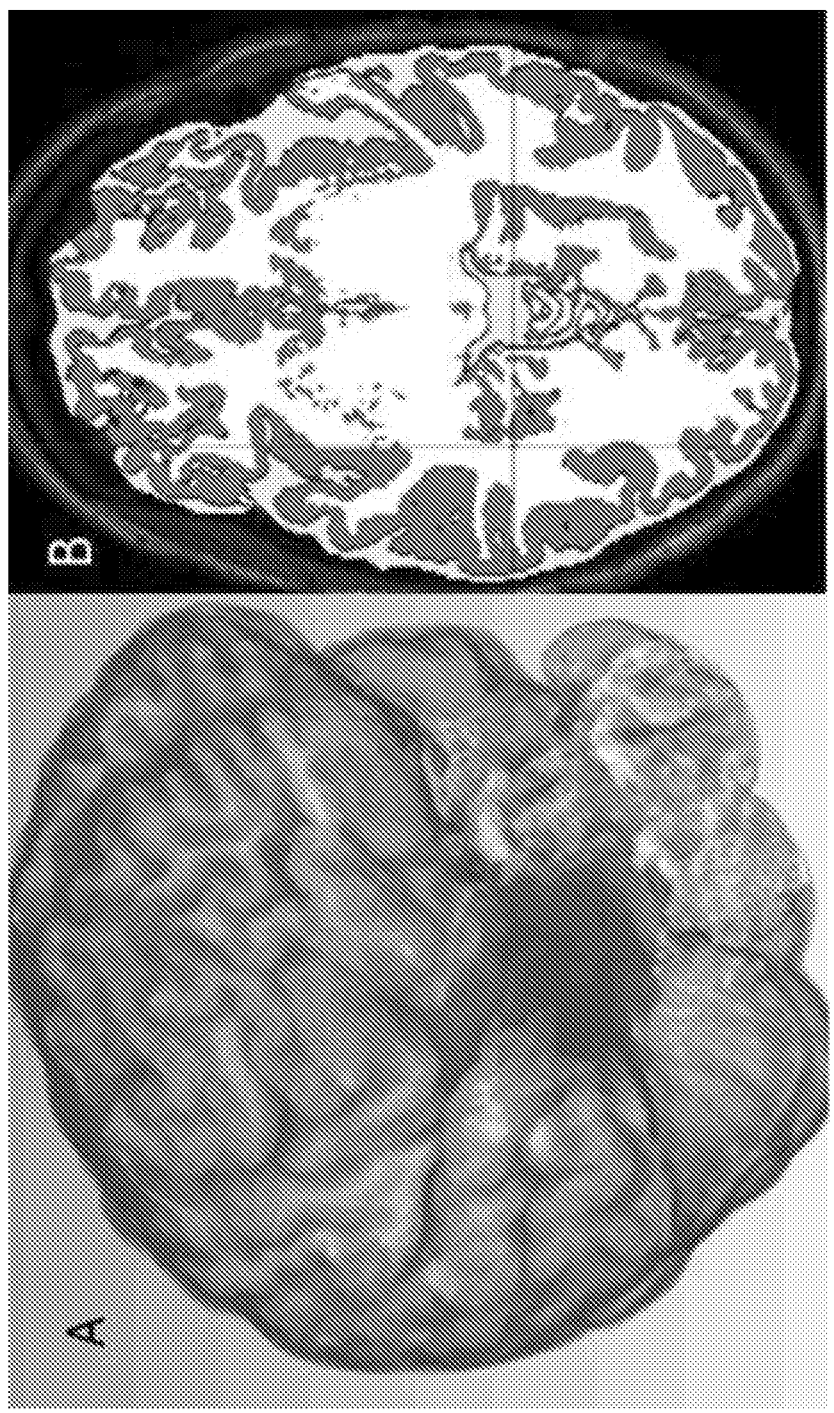
FIG. 3 are illustrations of a MRI 3D computational model. (A) The structural MRI was used to create a 3D computational model from the patients. (B) Segmentation of the subjects' MRI dataset was performed manually by using colored masks. (blue (light Grey)=CSF, grey=Grey matter, white=White matter)

The structural MRI was used to create a 3D model from the brain tissue using ScanIP (Simpleware Ltd v6.0, Exeter, UK). Segmentation of CSF, grey, and white matter was performed manually by creating masks using solid color flood-filled regions (FIG. 3).

Figure 4:
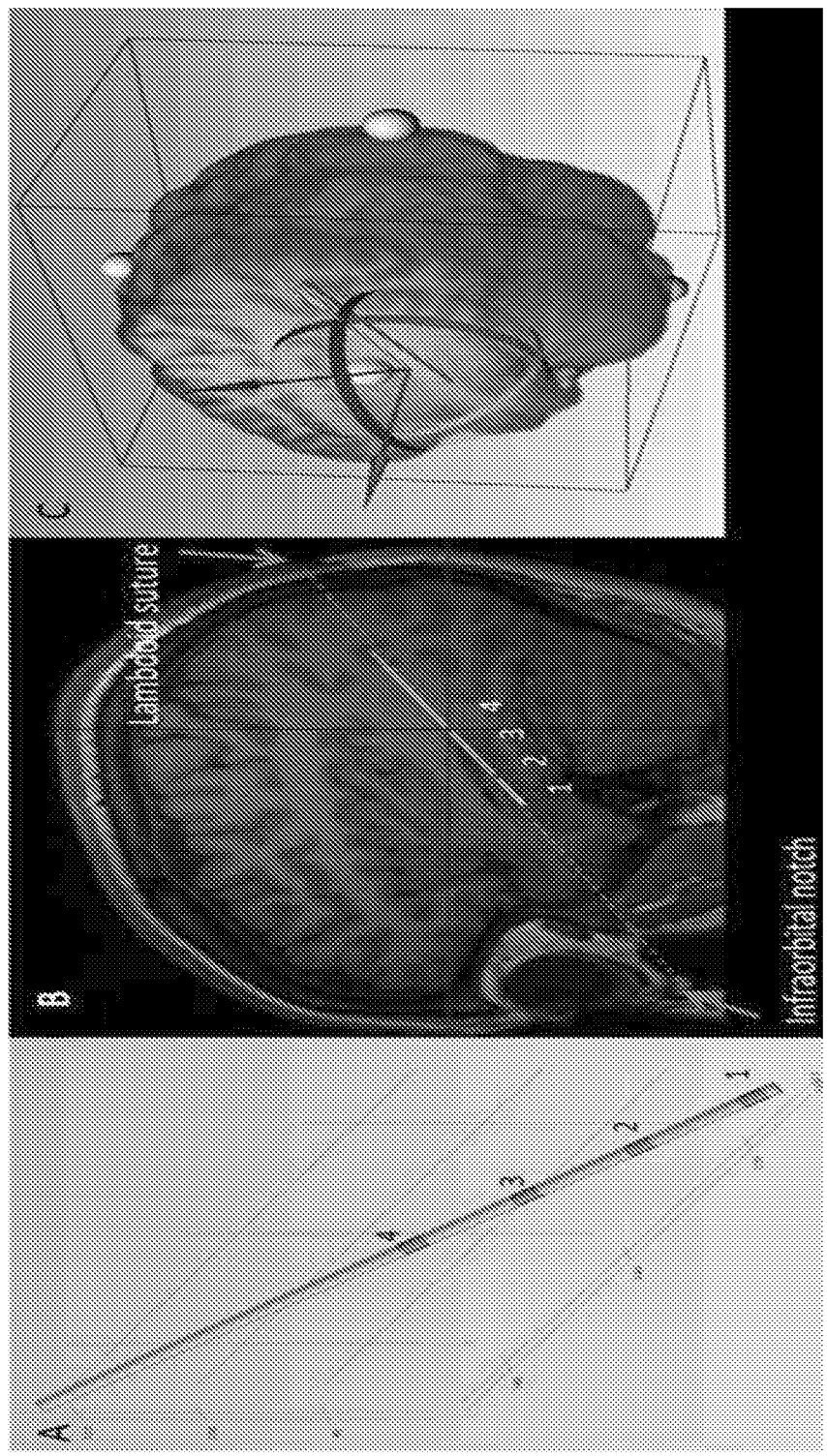
FIG. 4 are illustrations of a CAD electrode model. (A) The CAD electrode model consists of four conductive cylinders (1.27 mm diameter X 0.2 mm height) separated by insulators (10 mm between cylinder midpoints) The numbers in the figure indicate the depth electrode conductors from anterior to posterior. (B and C) Simpleware +CAD module is used to place the electrode in temporal lobe white matter.

Further resampling of the structural image may be performed through a linear interpolation method between neighbor voxels to generate cubic voxels of 0.2 mm. This resolution was necessary to include the depth electrode model. This model was constructed according to geometric specifications given by NeuroPace™ in a CAD platform. Specifically, consisting of four platinum/iridium conductive cylinders (1.27 mm diameter×2 mm height) separated by insulators (10 mm between the midpoints of the cylinders) (FIG. 4A) (Rossi, et al. "Predicting white matter targets for direct neurostimulation therapy", Epilepsy Research 91, 176-186 (2010). This CAD model was later placed in white matter in a strategic anatomical position within 4-5 mm of the grey-white matter interface using Simpleware +CAD module, FIGS. 4 B and C.

The electrode placement method disclosed above may be modified for the treatment of a tumor of the brain. Here, instead of acquiring the interictal and post-ictal datasets disclosed above, a baseline diffusion tensor imaging MRI dataset or a baseline single-photon emission computed tomography dataset is obtained from the brain of the patient and the position of the tumor determined from such a scan. A plurality of virtual electrode placement positions for an electrode are determined based on the tumor position, a VOCA calculated at each of a plurality of virtual electrode placement positions using the method disclosed above and based on the tumor position and the virtual electrode placement position. Of course, and isotropic or an anisotropic model may be used. An implantation position for the electrode is selected from the plurality of virtual electrode placement positions based on the VOCA at the implantation position. The implantation position is selected to give a required (therapeutically effective) electrical pulse to the tumor. The electrode is implanted at the implantation position and an electrical current delivered from the electrode to the tumor tissue within the VOCA.

The method of treating a tumor may also include the delivery of a plurality of nano-electrodes to the region of the brain containing the tumor. Such nano-electrodes may extend the VOCA beyond the region of coverage by the electrode in the absence of the nano-electrodes. In some embodiments, the nano-electrodes may be steered to the required position by an electrical field generated by the electrode. In the course of treatment of the tumor, an electrical charge contained in the nano-electrode may be released by, for example, an electrical field generated by the electrode.

Nano-Electrodes

The system and method disclosed herein may be utilized in conjunction of any suitable nanoparticle that can be guided to a required position within the brain and/or that can extend the VOCA of an electrode to allow for the treatment of a condition such as a tumor or an epileptic condition. Examples of such nano-electrodes include the energy-releasing carbon nanotube transponders disclosed in co-pending patent application publication number 2012-0209344, entitled "ENERGY-RELEASING CARBON NANOTUBE TRANSPONDER AND METHOD OF USING SAME" published Aug. 16, 2012, the contents of which are incorporated by reference.

In one embodiment, these transponders may include at least one carbon nanotube connected to a nanocapacitor. Optionally, a nanosensor is formed by at least one biomolecule ligand covalently attached to an end of at least one carbon nanotube. The nanocapacitor is connected to the opposite end of at least one of the carbon nanotube. The transponder is optionally coated with at least one biocompatible molecule to form a biocompatible coating. The transponder is optionally labeled with at least one molecular label.

The transponder may release a biologically non-destructive electric charge to target cells or, alternatively, may release a biologically destructive electric charge to target cells. In general, a biologically non-destructive electric charge is used in the treatment of epilepsy while a biologically destructive electric charge is used in the treatment of a tumor.

Figure 6:
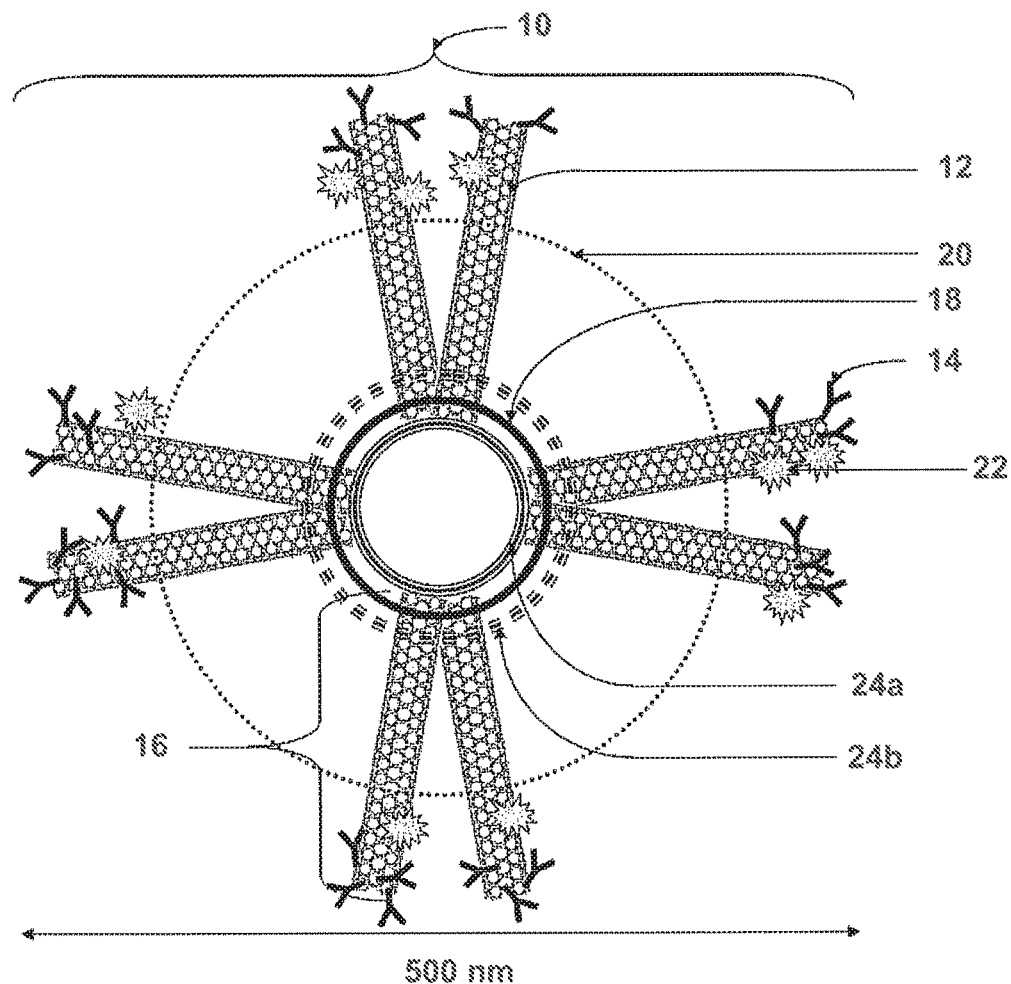
FIG. 6 is a diagram of one embodiment of an energy-releasing carbon nanotube transponder FIG. 7 (A) is a schematic illustration of a raw metallic-type carbon nanotube is depicted in side (left) and axial (center) views. Carbon nanotubes cross-linked to fluorescein isothiocyanate (FITC) are shown (right) via a zero-length amide bridge during the functionalization process.

Turning now to FIG. 6. This figure illustrates one embodiment of the energy-releasing carbon nanotube transponder. The energy-releasing carbon nanotube transponder 10 integrates at least one carbon nanotube 12 attached to a nanocapacitor 18. Optionally, the energy-releasing carbon nanotube transponder 10 also integrates at least one carbon nanotube 12 attached to a biomolecule ligand 14 in order to form a nanosensor 16 subassembly. Optionally, the energy-releasing carbon nanotube transponder 10 also integrates at least one carbon nanotube 12 attached to a molecular label 22. Optionally, a coiled nanowire located inside (24a) the nanocapacitor 18, or alternatively by design, outside (24b) the nanocapacitor 18, allows for the energy-releasing carbon nanotube transponder 10 to be recharged in energy once it has been discharged.

The response of a nanosensor 16 involves three characteristics; 1) the electrostatic interaction between the net charge of a biomolecule, a carbon nanotube and counter ions in buffer; 2) movement or transport of the biomolecule to a receptor or marker and 3) alteration of the conductance of the carbon nanotube 12. For example, a nanosensor 16 formed by the attachment of a biomolecule ligand 14 to a carbon nanotube 12 can be introduced into one or more epileptic circuits to detect changes during seizure activity (e.g., femtomolar increases in the neurotransmitter glutamate correlates to an increased conductivity of the carbon nanotube 12 of the nanosensor 16. A detection threshold of the energy-releasing carbon nanotube transponder 10 can be used to discharge a nanocapacitor 18 to deliver direct stimulation therapy to potentially stabilize the epileptic circuit.

A capacitor functions much like a battery but charges and discharges much more efficiently. A nanocapacitor 18 is a nanostructure large enough to connect to at least one carbon nanotube 12. The nanocapacitor 18 has a capacity for storing an electric charge appropriate to its application. The method of charging the nanocapacitor 18 is according to the requirements of the particular nanocapacitor 18. An example of a suitable nanocapacitor can be provided by a nanotechnology company such as SolRayo, Inc, Madison, Wis. Optionally, a coiled nanowire located inside (24a) the nanocapacitor 18, or alternatively by design, outside (24b) the nanocapacitor 18, allows for the energy-releasing carbon nanotube transponder 10 to be recharged in energy once it has been discharged.

In the first exemplary embodiment, the nanocapacitor 18 and the energy-releasing carbon nanotube transponder 10 release biologically destructive electric charge densities in the range of between about 21 and about 30 microCoulombs/cm$^2$ and preferably about 23 microCoulombs/cm$^2$. In the second exemplary embodiment, the nanocapacitor 18 and the energy-releasing carbon nanotube transponder 10 release biologically non-destructive electric charge densities in the range of between about 4 and about 20 microCoulombs/cm$^2$.

Optionally, a biocompatible coating 20 surrounds the energy-releasing carbon nanotube transponder 10, for example, to improve bio tolerance and/or adherence of the energy-releasing carbon nanotube transponder 10 onto target cells. For example, the nanotransponder presently disclosed can be coated with an amphilic copolymer that can enhance biocompatibility of the nanodevice. In other embodiments, the biocompatible coating is a material selected from PEG, polylactic acid (PLA), polyglycolic acid (PGA), poly lactide co-glycolide (PLGA) or chitosan or combinations of at least two of these materials.

Example 1—Characterization of Carbon Nanotubes

Figure 7A:
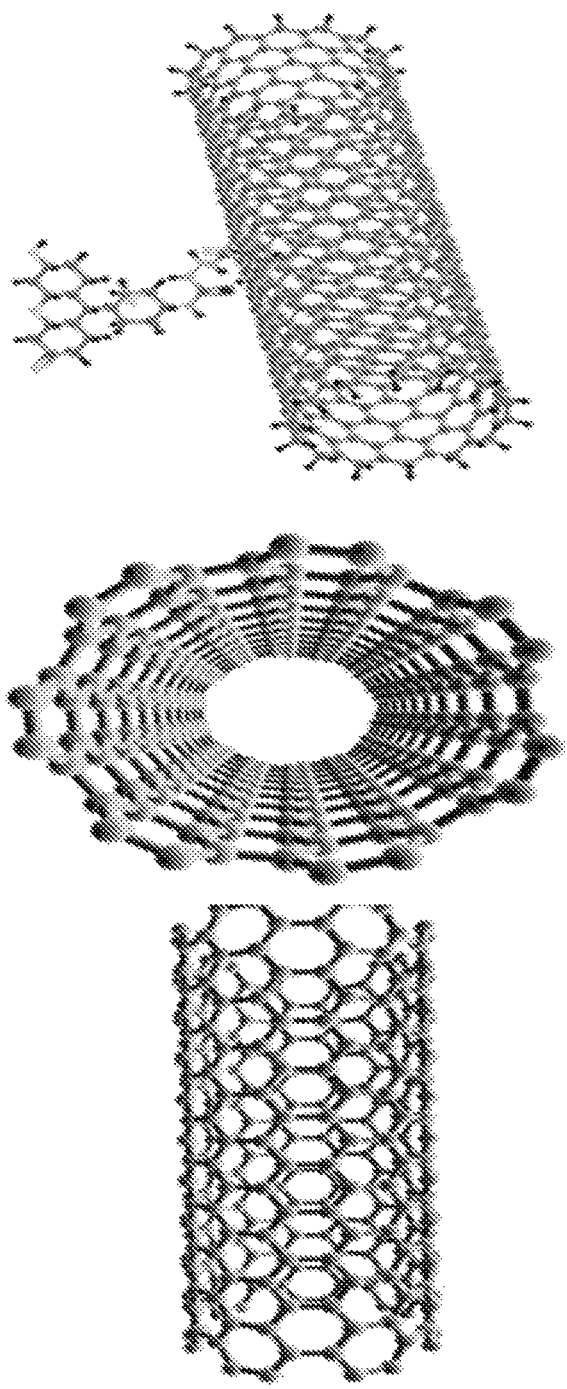
FIGS. 7(B)(i)-(iii) illustrates the characterization of various purities of carbon nanotubes via Fourier Transform Infrared (FTIR) spectroscopy using attenuated total reflectance (ATR).
Figure 7B:
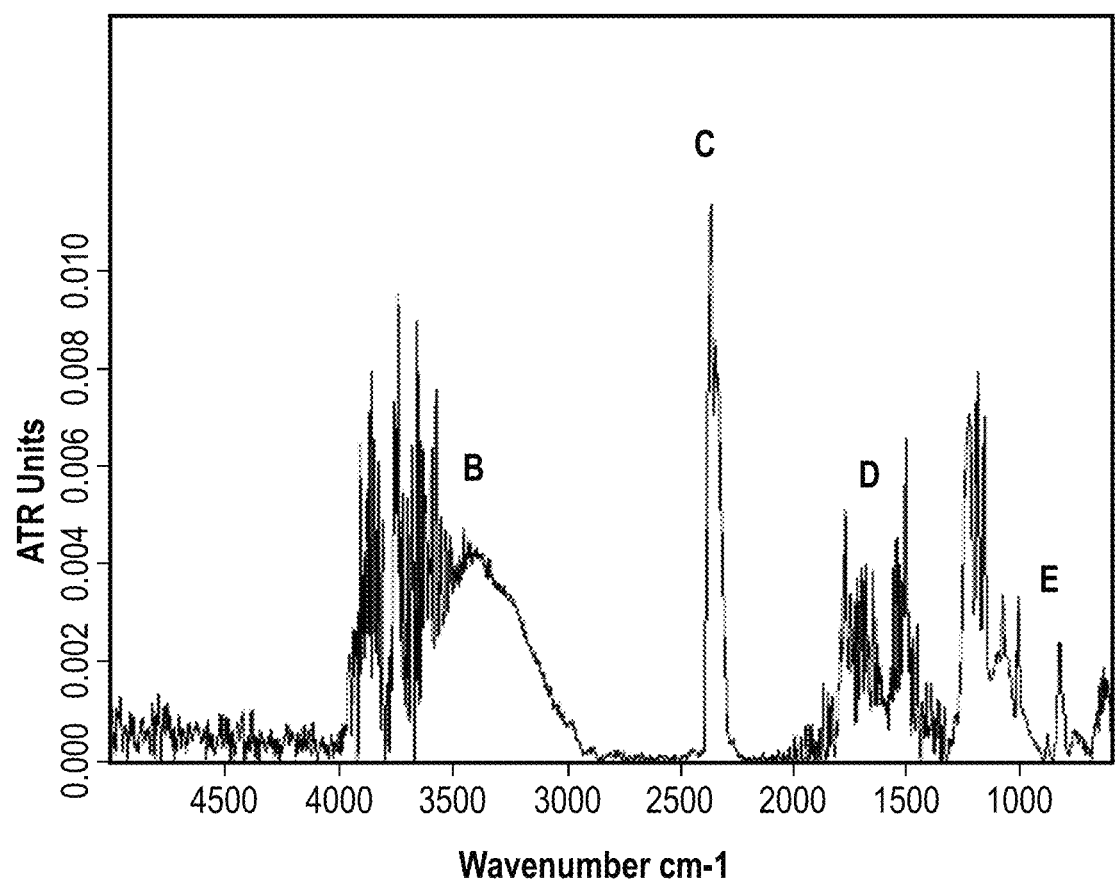
Figure 8:
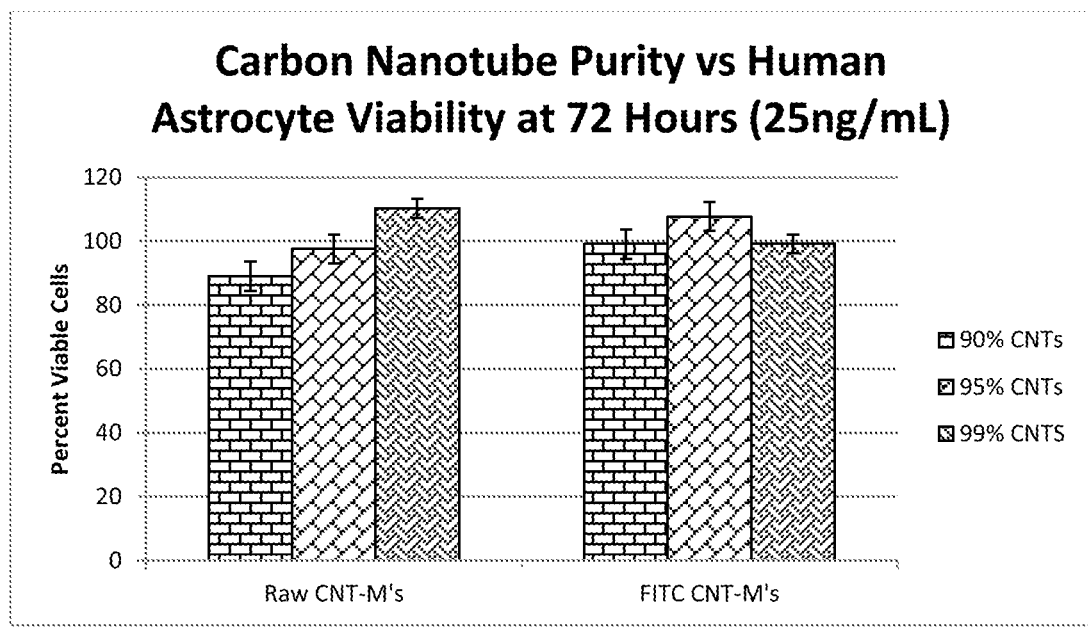
FIG. 8 is a graph illustrating the results of in vitro cytotoxicity testing of carbon nanotubes.

Raw metallic-type carbon nanotubes (CNTs) cross-linked to fluorescein isothiocyanate (FITC) (illustrated in FIG. 7(A)) are characterized for various impurities via Fourier Transform Infrared (FTIR) spectroscopy using attenuated total reflectance (ATR). FIGS. 7(B)(i)-(iii) shown the characterization for 90% Metallic-Type CNTs+FITC (7(B)(i)), 95% Metallic-Type CNTs+FITC (7(B)(ii)) and 99% Metallic-Type CNTs+FITC (7(B)(iii). The following peaks are shown—A: hydroxyl peak from COOH and atmospheric $H_2O$. B: Atmospheric $CO_2$. C: C=O from carboxylic acids/derivates. D: C=C from alkenes. E: Substrate-specific fingerprint region.

Example 2—In Vitro Cytotoxicity Testing of Carbon Nanotubes

To confirm that CNTs could be safely used in the brain, Human Astrocytes (HA) isolated from the cerebral cortex were obtained from ScienCell Research Laboratories (Carlsbad, Calif. 92011) and cultured per ATCC protocols. The HA's were treated with both raw and chemically-functionalized metallic-type CNTs (CNT-M) of 90 (left bars), 95 (center bars), and 99 (right bars) percentage purity. Cell viability was measured after 72 hours via an alamar blue assay. Upon performing a two-tailed student's t-test ($\alpha=0.05$), the HA viability testing determined that 90% pure raw metallic-type CNTs reduced HA viability relative to 99% pure metallic-type CNTs at 25 ng/mL. No statistically significant difference in HA viabilities was observed once the CNTs were functionalized.

Figure 9A:
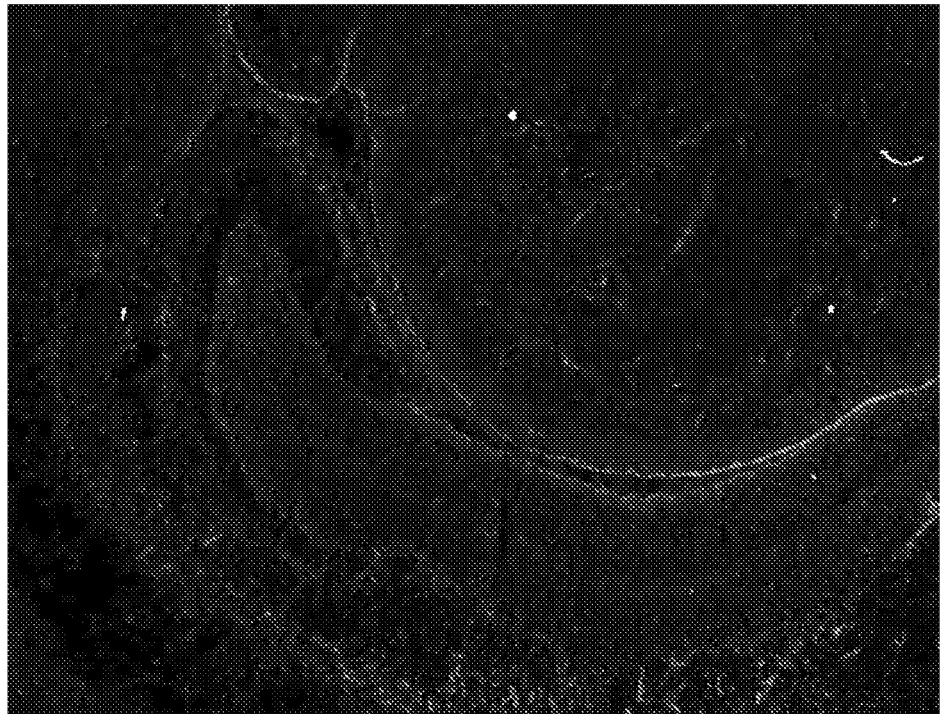
FIGS. 9(A) and 9(B) show immunofluorescent staining to observe the influence of 99% pure FITC-functionalized CNTs injected stereotactically into the left hippocampal formation of a Rowett rat.
Figure 9B:
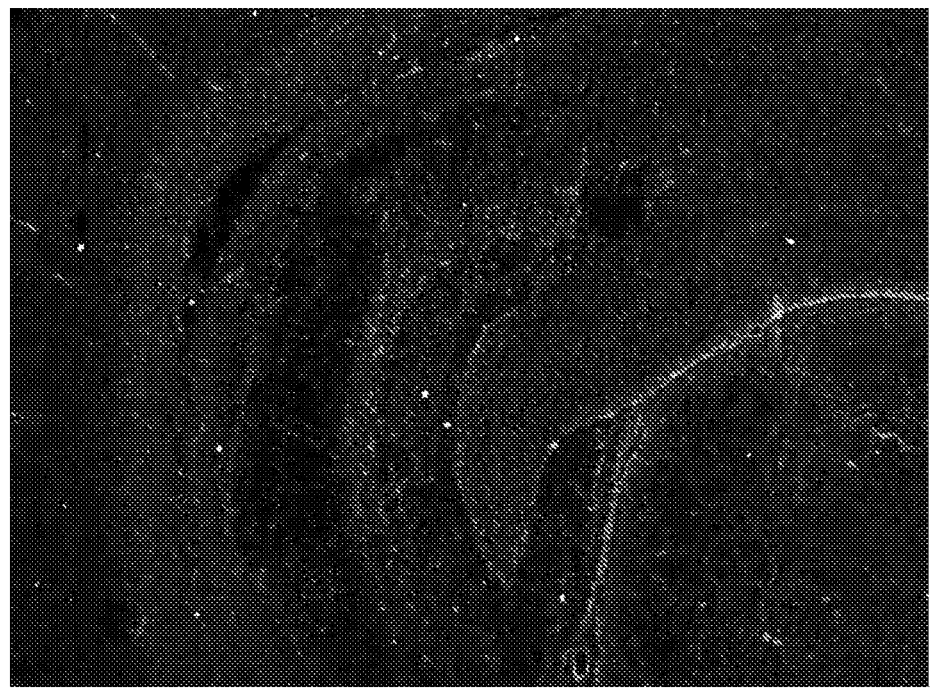
Figure 9C:
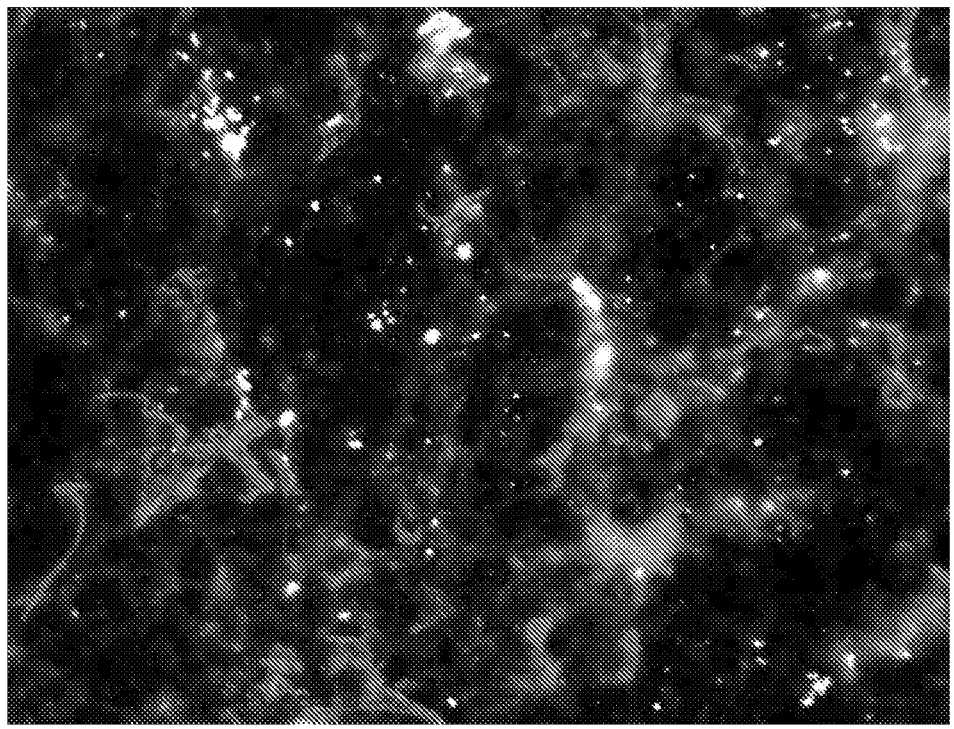
FIGS. 9(C) and 9(D) depict a 100× magnification of part of the views in FIGS. 9(A) and 9(B) respectively.
Figure 9D:
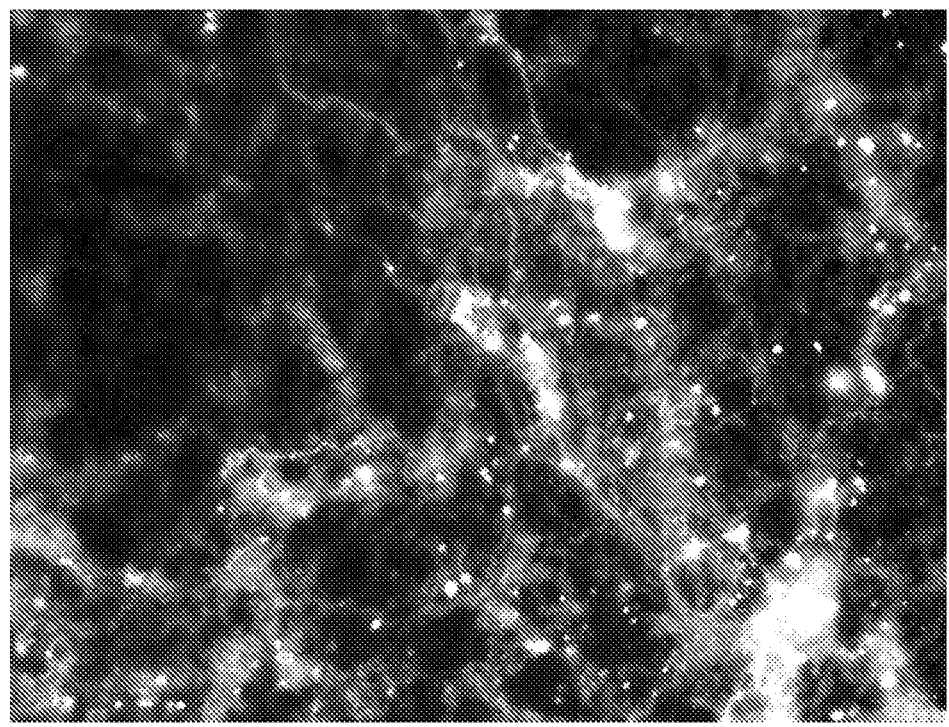

Example 3—Influence of 99% Pure FITC-Functionalized CNTs Injected Stereotactically Immunofluorescent staining was performed to observe the influence of 99% pure FITC-functionalized CNTs ("CNT-M") injected stereotactically into the left hippocampal formation of a freely moving Rowett rat 4 weeks prior to sacrifice. Per standard protocols, astrocytes were labeled in fresh frozen 20 micron thick sections via GFAP using secondary antibody with Cy5 (649 nm λ). The right hippocampal formation FIG. 9(A) was injected with distilled PBS (magnification 2×). The left hippocampal formation at the dentate gyrus FIG. 9(B) was injected with 1 μL of 25 ng/mL 99% pure FITC-functionalized CNTs (magnification 2×). FIGS. 9(C) and 9(D) depict a 100× magnification of a region of FIGS. 9(A) and 9(B) respectively.

Example 4—Delivery of Signal Waveform

Figure 10A:
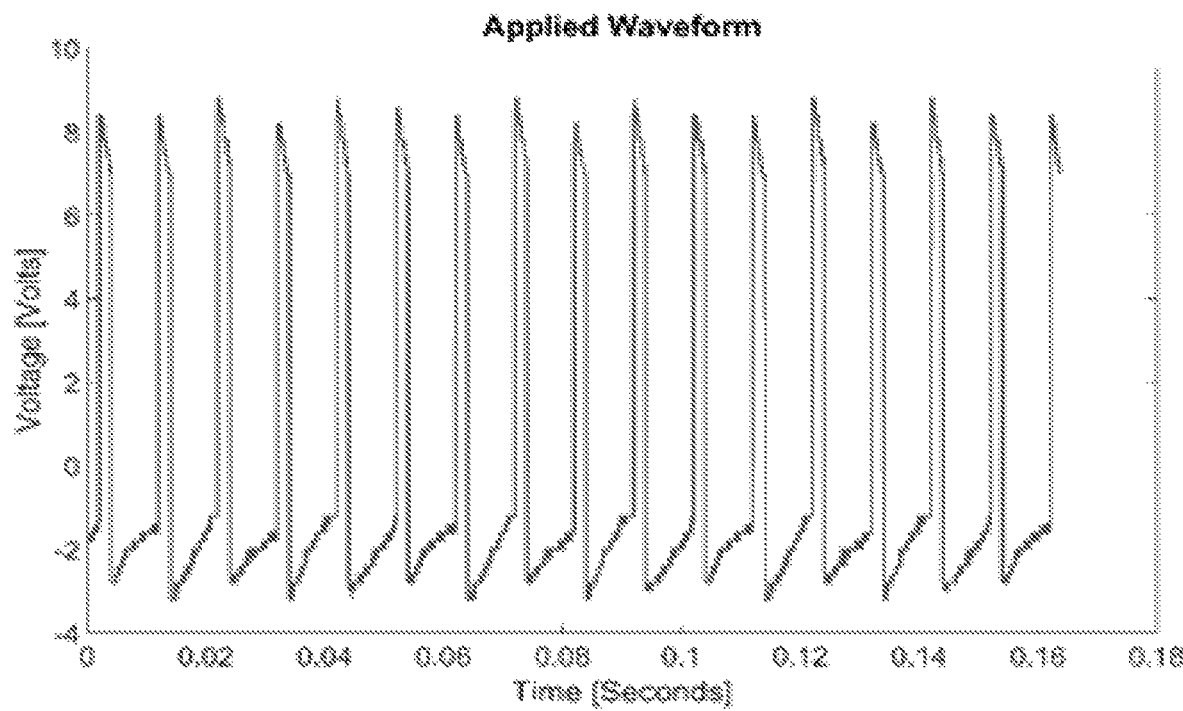
FIGS. 10(A)-(D) illustrates a 100 Hz, asymmetric, charge-balanced +10V, −2.5V signal waveform FIG. 10(A) delivered to an agarose gel brain phantom FIG. 10(B). A schematic of the five 1 μL injections of 0.25 ng/mL of 95% pure FITC-functionalized metallic-type carbon nanotubes is depicted in FIG. 10(C).
Figure 10B:
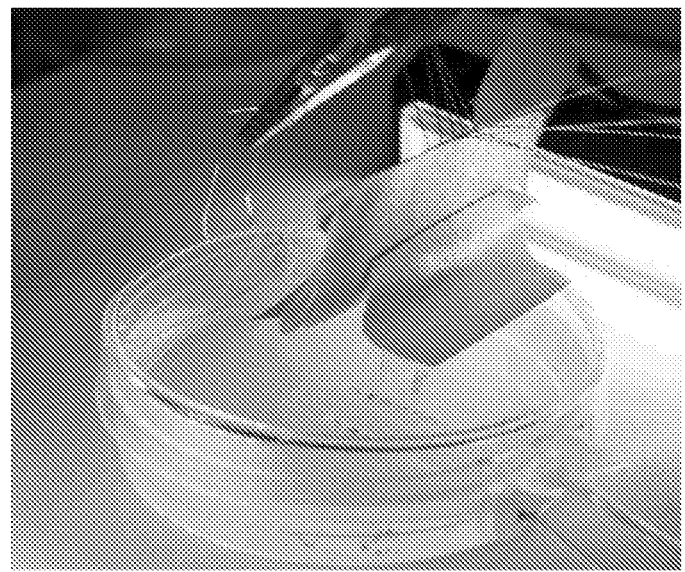
Figure 10C:
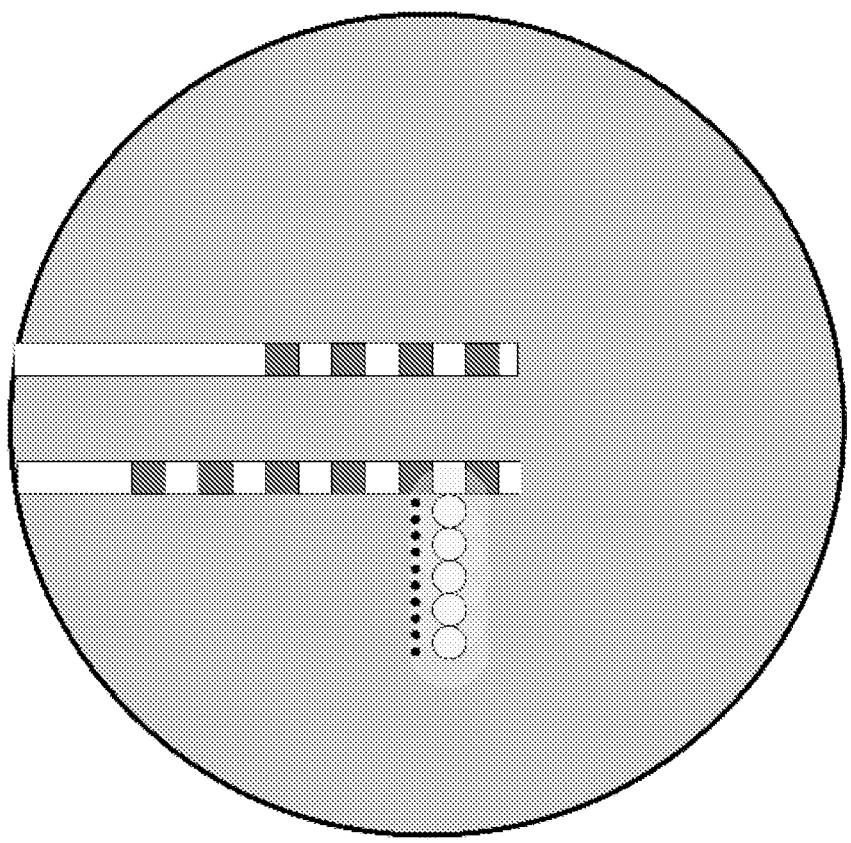
Figure 10D:
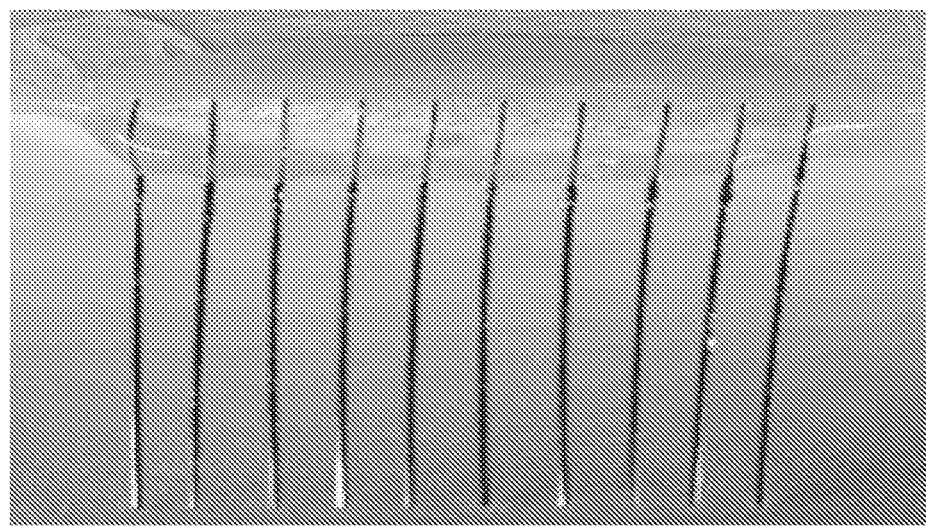
Figure 11A:
FIGS. 11(A)-(B) illustrate the construction of a Finite Element Method (FEM) mesh. The depth lead shown in FIG. 11(A) was used as the basis for the mesh shown in FIG. 11(B).
Figure 11B:
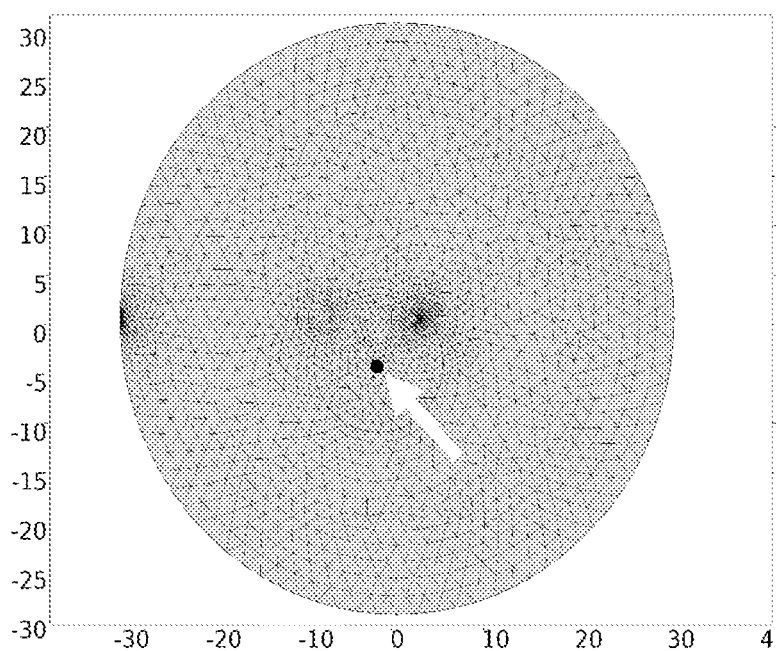

A 100 Hz, asymmetric, charge-balanced +10V, −2.5V signal waveform FIG. 10(A) was delivered via an AM-Systems 3800 stimulator through the 1.1 mm diameter AD-Tech depth lead. The lead was cast in 0.6% Type VII agarose gel brain phantom FIG. 10(B). A schematic of the five 1 μL injections of 0.25 ng/mL of 95% pure FITC-functionalized metallic-type carbon nanotubes is depicted in FIG. 10(C). The recording electrode was composed of 0.005" 316L stainless steel FIG. 10(D).

Example 5—Construction of a Finite Element Method (FEM) Mesh

The experimental set up of a depth lead FIG. ñ(A) was used as the basis for a Finite Element Method (FEM) mesh shown in FIG. ñ(B). The arrow depicts the area of the mesh which was modified to match the approximated conductivity value of a diffused sample of CNT-M's which follow a Gaussian distribution of conductivity originating at the injection point. This 4767-element triangular mesh was subsequently used to solve the Poisson's Equation computationally for the electric potential using COMSOL Multiphysics.

Figure 12A:
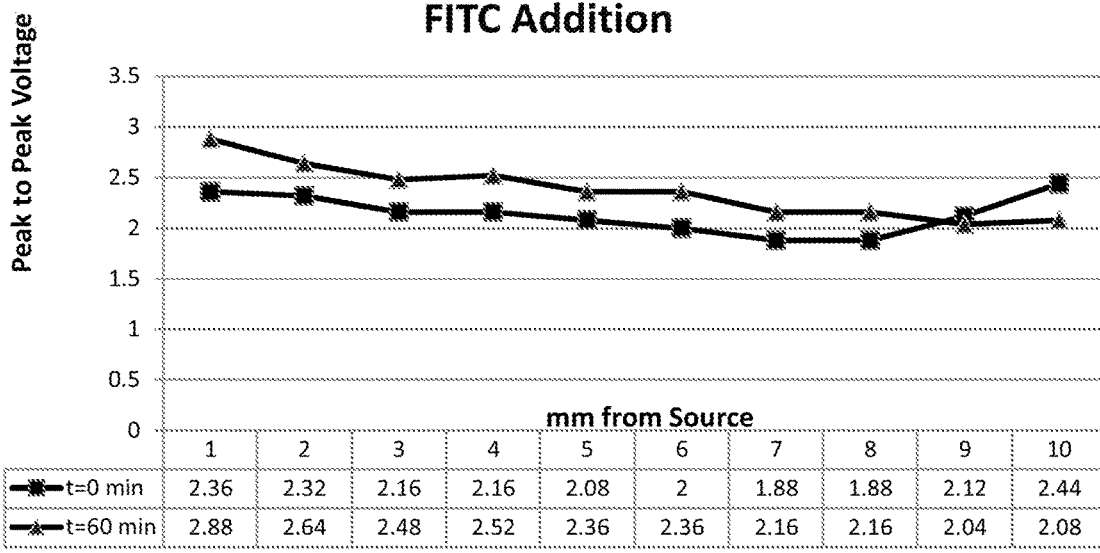
FIG. 12(A) is a graph illustrating the baseline voltage drop within a 0.6% agarose gel phantom was measured immediately prior to administering five 1 μL injections of 25 ng/mL 95% FITC-functionalized CNT-Ms. T=0—lower graph; t=60 min—upper graph.
Figure 12B:
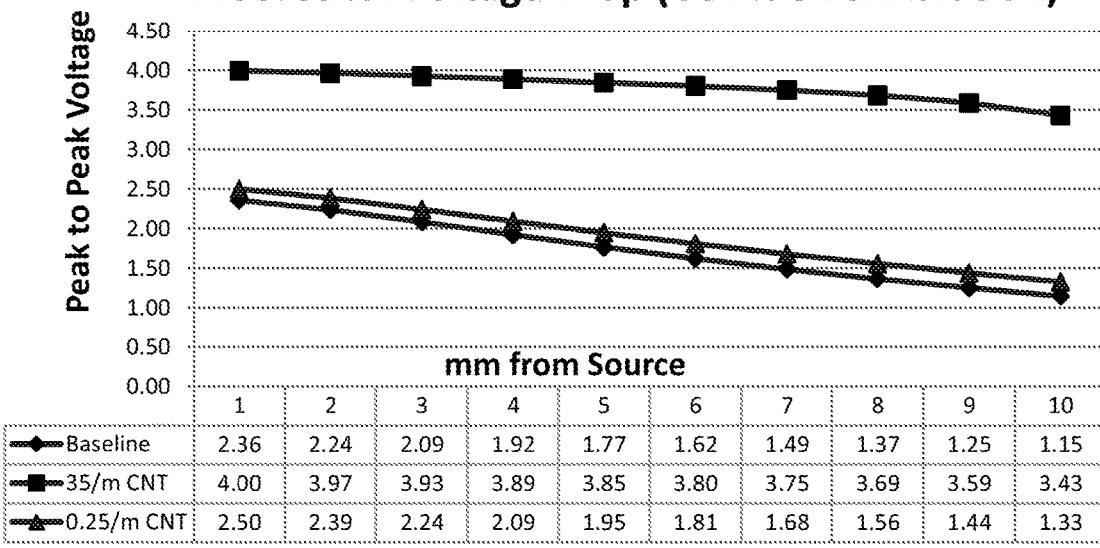
FIG. 12(B) is a graph illustrating a FEM simulation of the voltage drop within an agarose gel phantom. Baseline—lower graph; 3 S/m CNT—upper graph; 0.2 S/m CNT—middle graph.

Example 6—Carbon Nanotubes Cause a Baseline Voltage Drop within an Agarose Gel The baseline voltage drop within a 0.6% agarose gel phantom was measured immediately prior to administering five 1 μL injections of 25 ng/mL 95% FITC-functionalized CNT-Ms as illustrated in FIG. 12(A). After allowing the CNT-Ms to diffuse for 60 minutes, the voltage drop was re-measured to determine the influence of the CNT-Ms within a brain phantom. A paired two-tailed student's t-test ($\alpha=0.05$) was performed and demonstrated that the CNT-Ms had a statistically significant ($p=0.02$) difference on the voltage drop within the brain phantom. This finding was computationally consistent with the FEM simulation of the voltage drop within an agarose gel phantom FIG. 12(B). This computational model demonstrated that as local conductivities are increased, the voltage change decreases.

Example 7—Effect of Carbon Nanotubes on Electric Potential

Figure 13A:
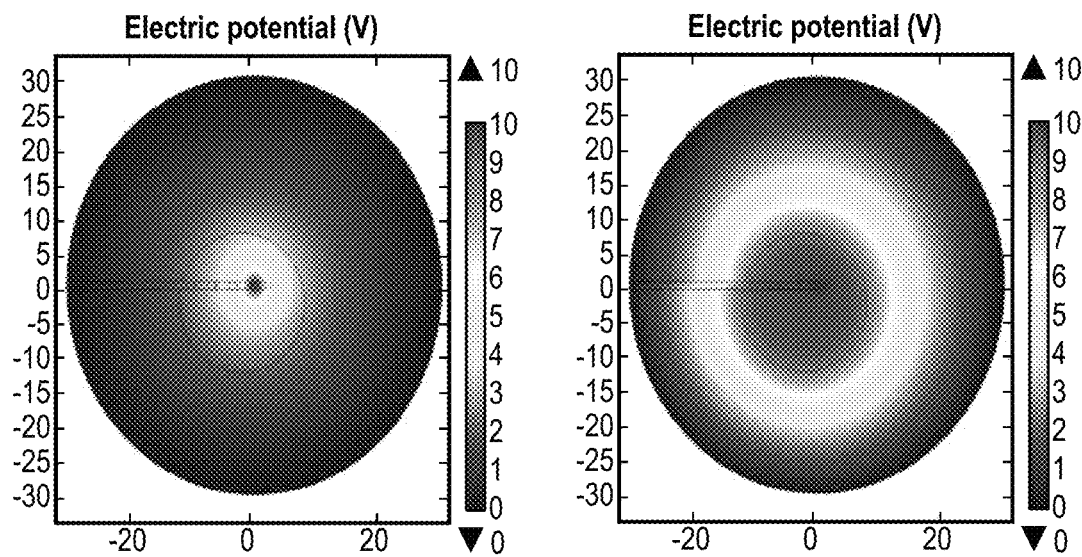
FIGS. 13(A) and (B) illustrate the effect of carbon nanotubes on electric potential.
Figure 13B:
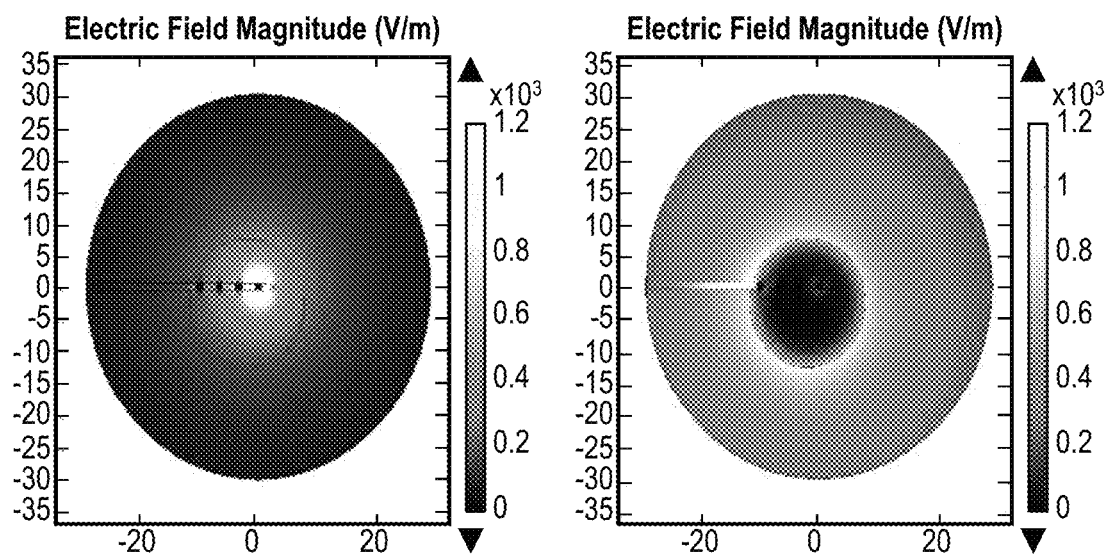
FIG. 13(B) illustrates a FEM simulation comparing a baseline profile (left) to a CNT-M modified conductivity model (right).

After allowing the CNT-Ms to diffuse for 60 minutes, the agarose gel phantom (FIG. 13(A)) was imaged with a UV transilluminator (Vernier) to determine the spread of the FITC-functionalized 95% CNT-Ms. A FEM simulation comparing a baseline profile (left) to a CNT-M modified conductivity model (right) is shown in FIGS. 13(B & C). These computational models demonstrate that within the area of CNT-M modified conductivity, the electric potential remains almost constant, see FIG. 13(B). While the electric field is almost zero within the conductive area, there is a sharp falloff at the boundary which may indicate activation at that location, see FIG. 13(C).

Figure 14A:
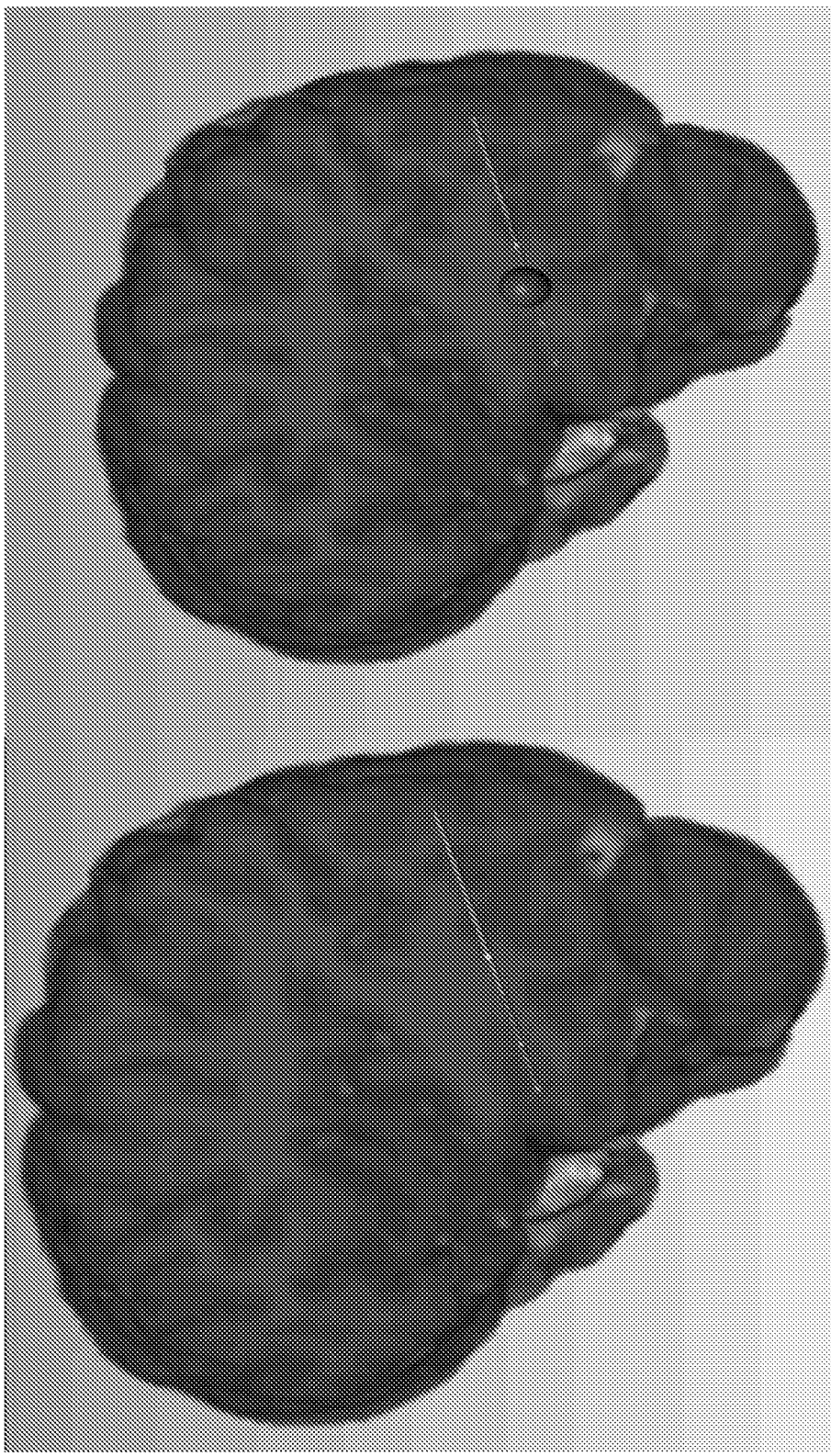
FIGS. 14(A)-(E) illustrate a 3D computational brain model constructed from structural MR-Images.
Figure 14B:
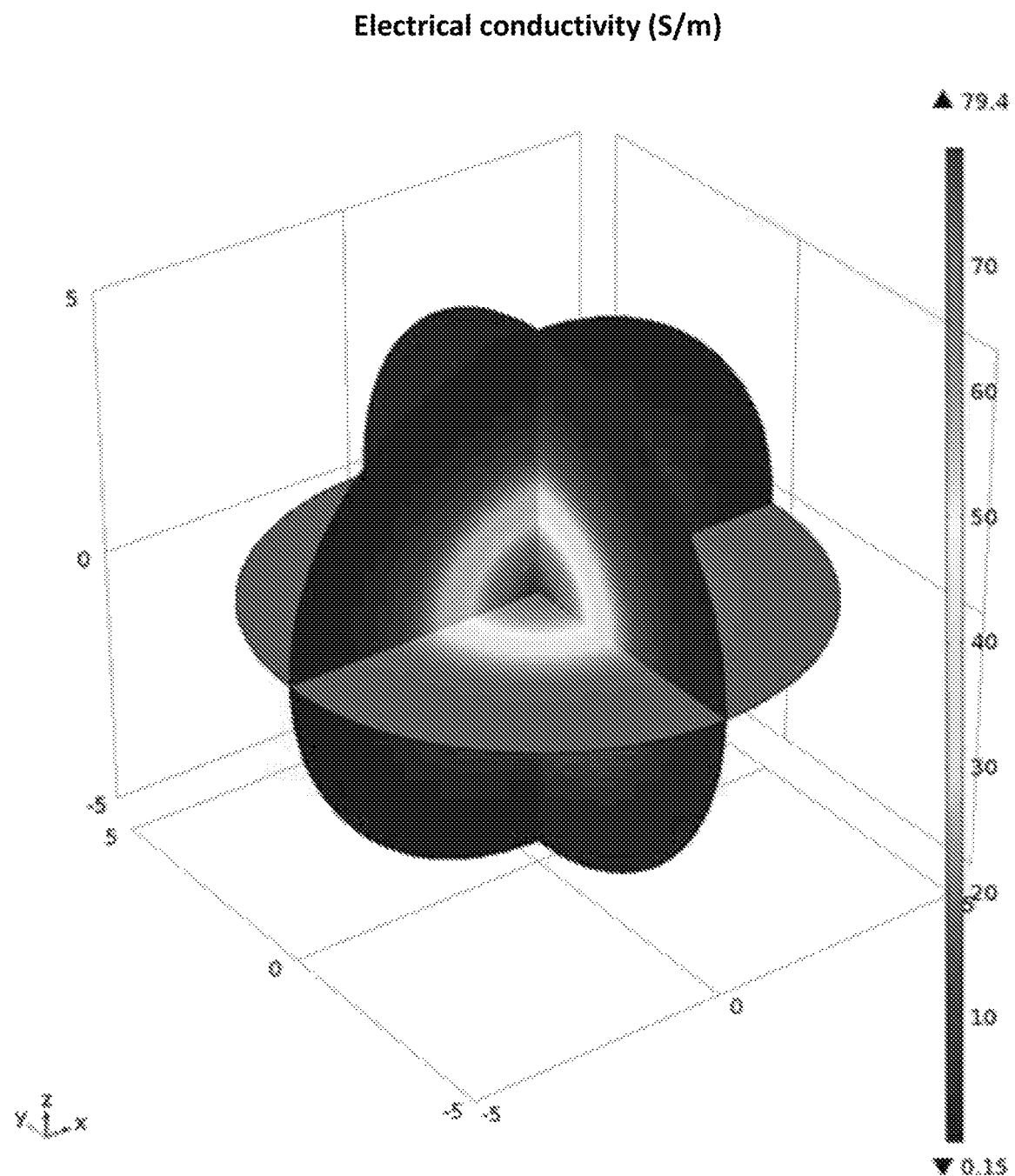
Figure 14C:
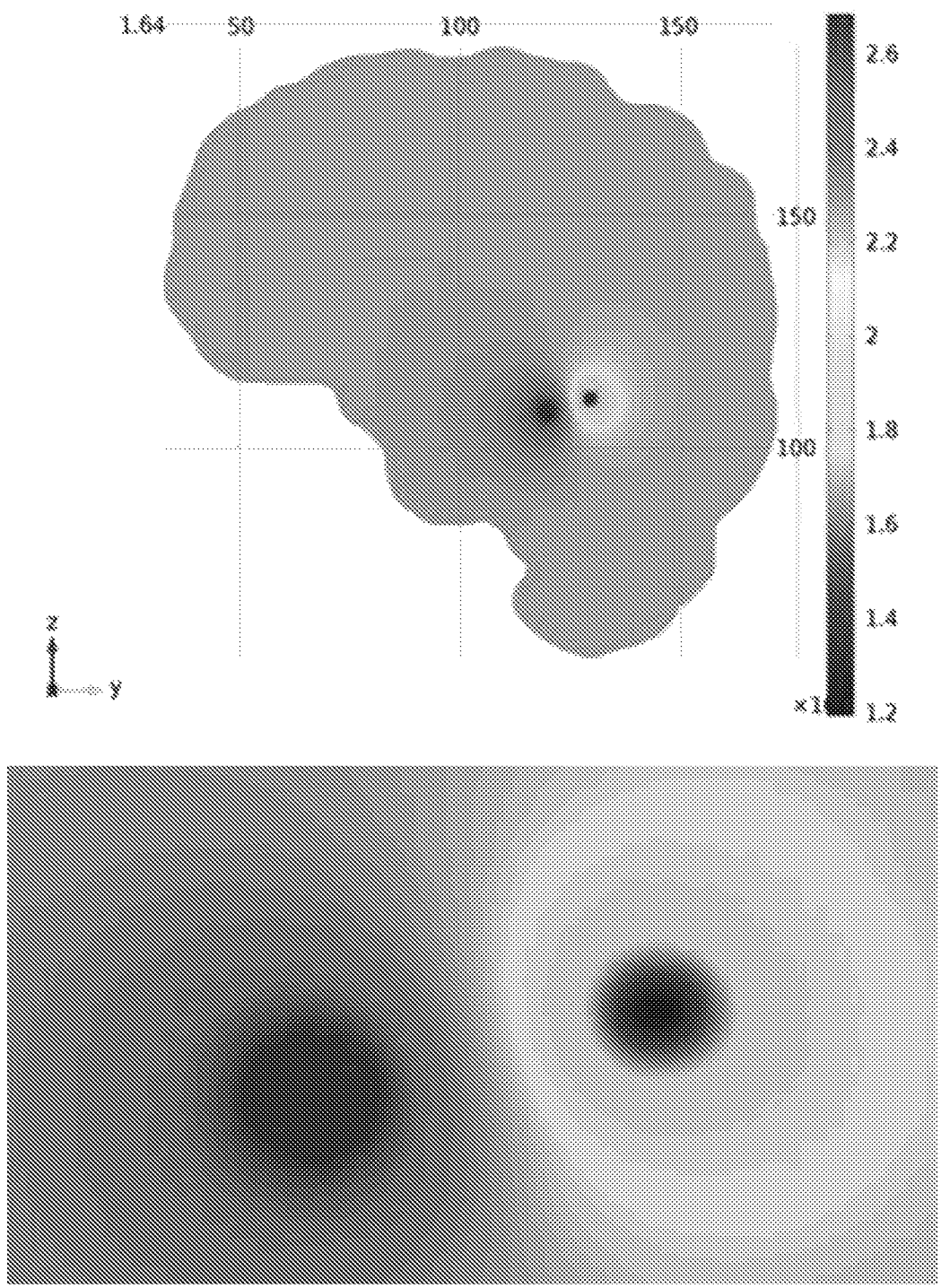
Figure 14D:
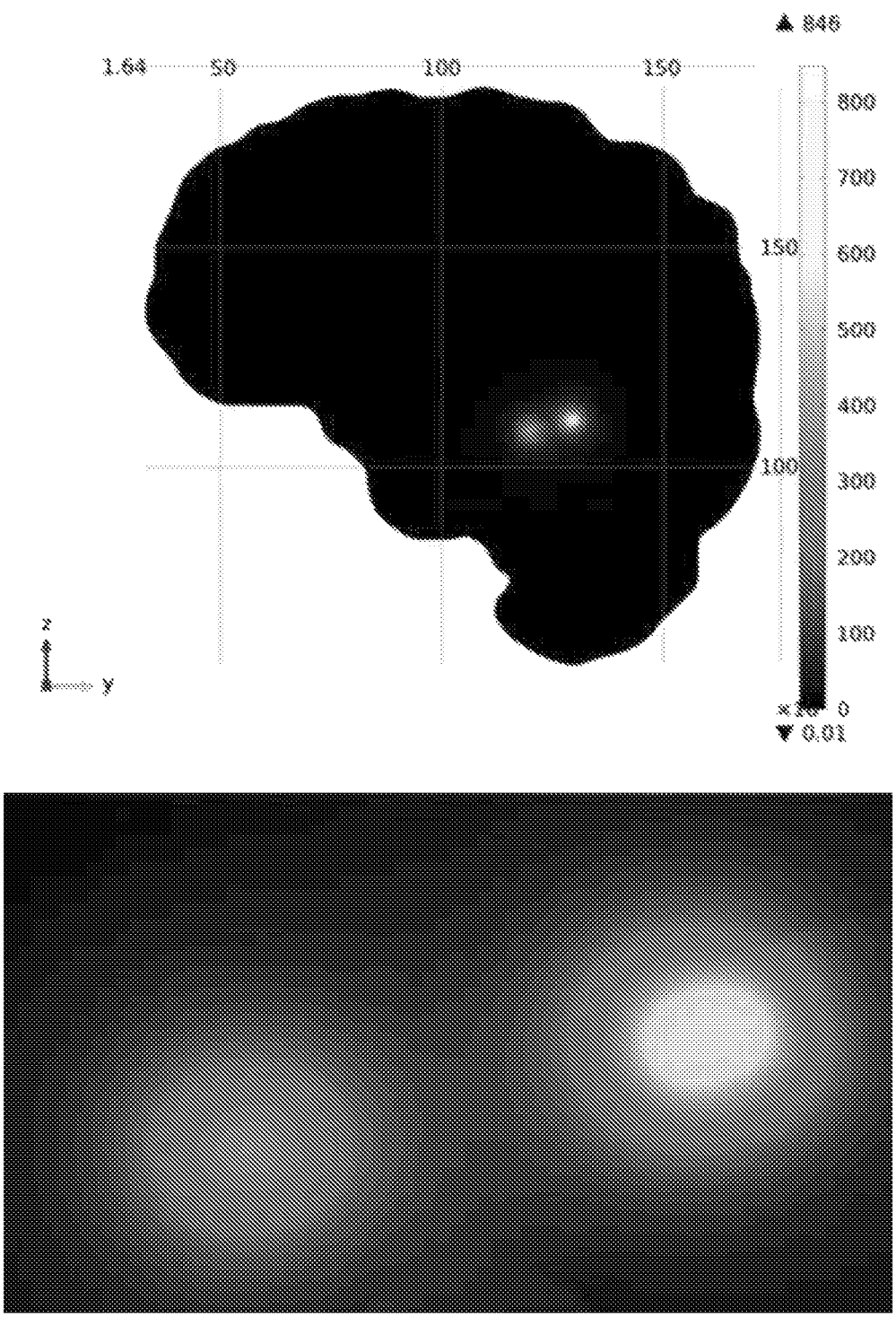
Figure 14E:
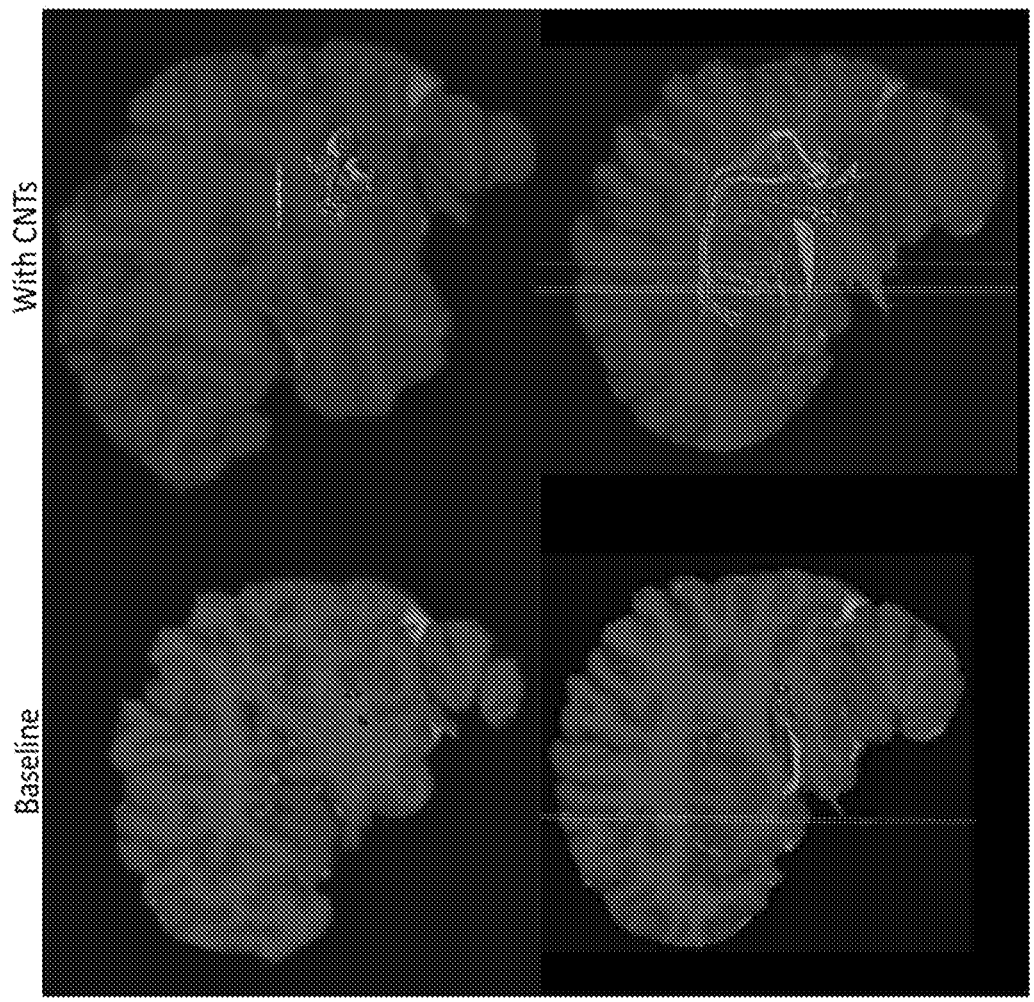

Example 8—A 3D Computational Brain Model was Constructed from Structural MR-Images Virtual electrodes were positioned within white matter that is adjacent to the hippocampal formation. A spherical geometry was added which modeled the increased conductivity due to CNT-Ms, see FIG. 14(A). This spherical volume of modified conductivity followed a Gaussian profile, see FIG. 14(B). A FEM simulation comparing the baseline profile to the CNT-M modified conductivity profile was numerically solved for the Electric Potential, see FIG. 14(C)(i) and (ii). This comparison showed that the CNT-M modified model maintains a uniform electric potential within the area of increased conductivity. This equipotential behavior produces an Electric Field approaching zero within the area of higher conductivity; however, at the boundary a sharp increase in Electric Field is observed, see FIG. 14(D)(i) and (ii). Using the results of the previous simulations, an activation function was calculated (Cendejas-Zaragoza et al, 2014; 2015). This function served as the seed for generating modulated circuit tractography (MCT) mapping of the axon bundles which could potentially be activated via a depth lead, see FIG. 14(E). The volume of cortical activation with CNT-M modified conductivity is substantially larger assuming sufficient current is supplied.

Example 9—Parametric Analysis of the Electric Potential

Figure 15A:
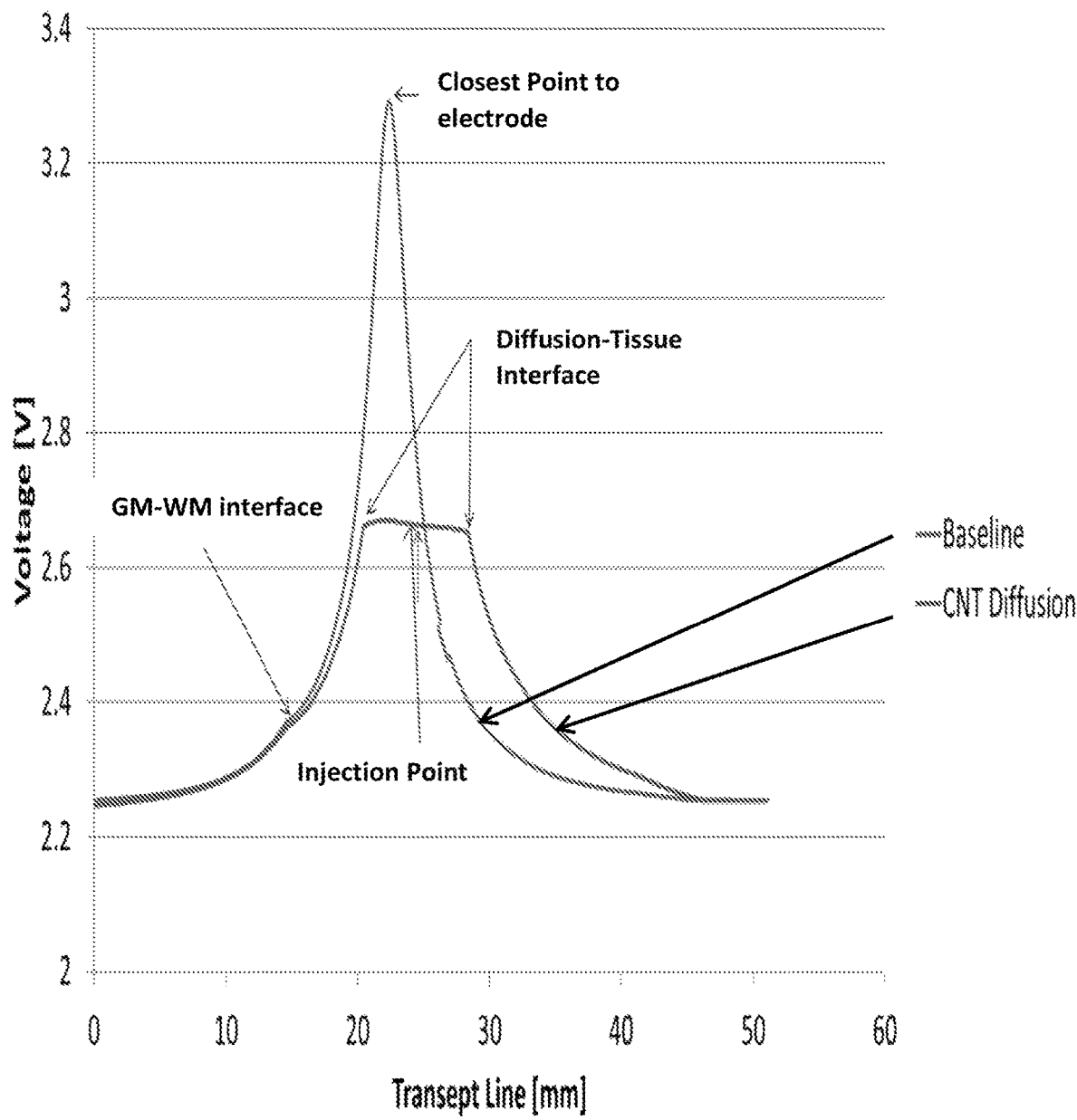
FIG. 15(A)-(C) illustrates a Parametric Analysis of the Electric Potential.
Figure 15B:
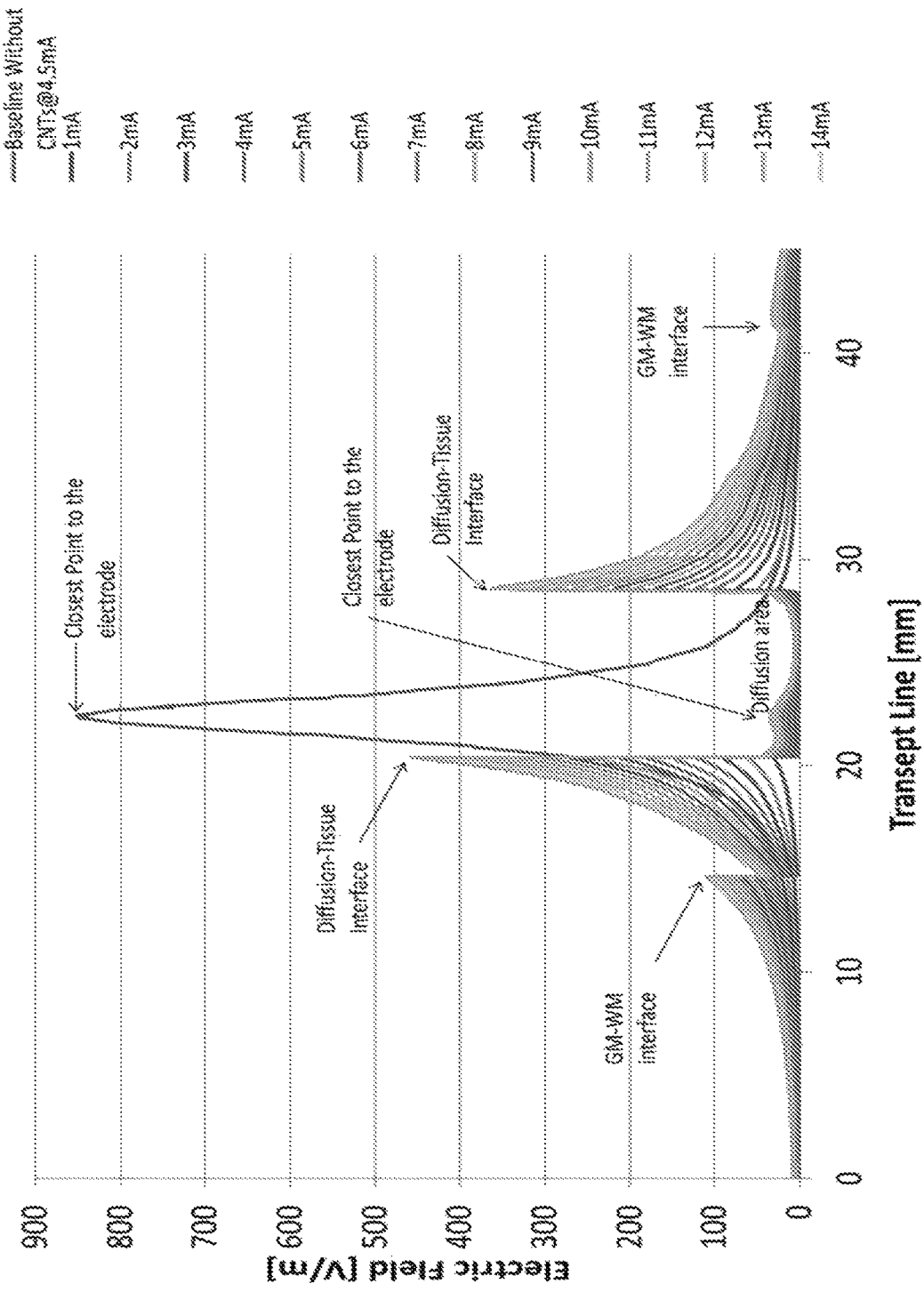
Figure 15C:
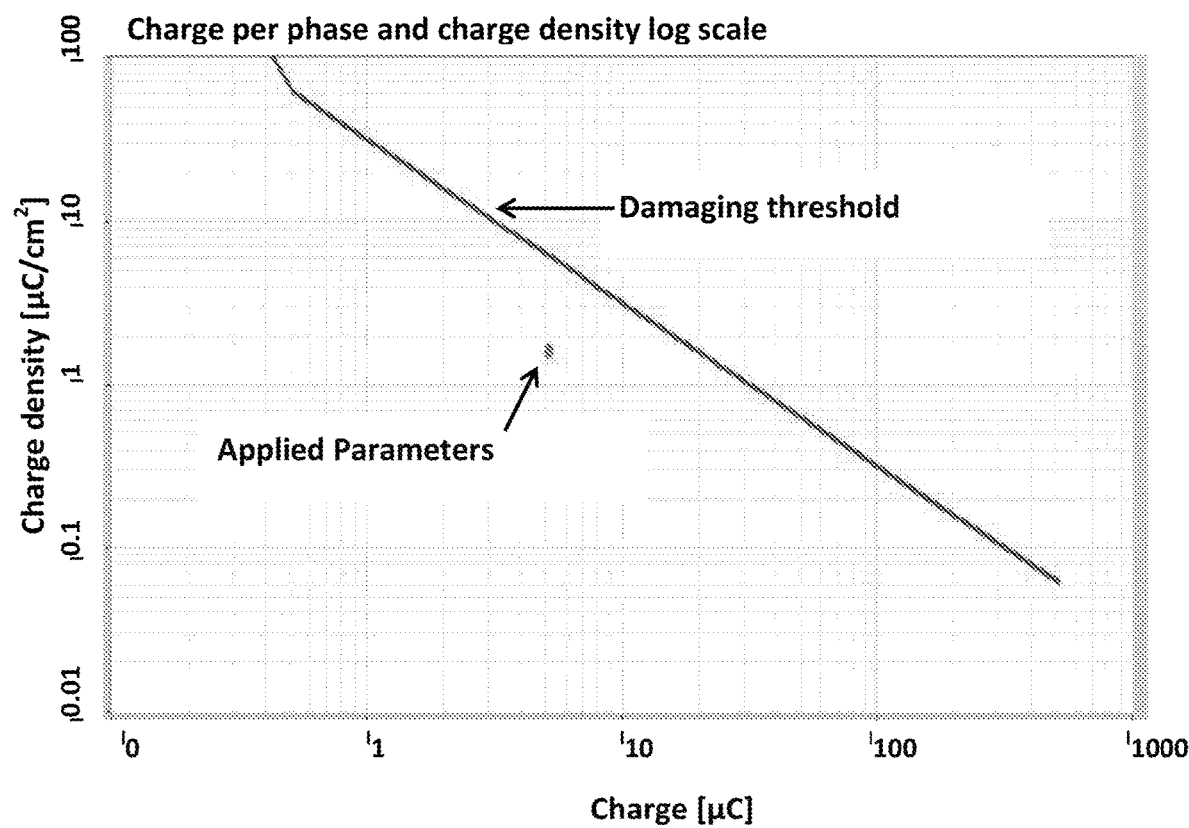

Parametric analysis of the electric potential in a transept line is drawn through the volume of CNT-modified conductivity compared to a baseline profile without CNT-Ms, see FIG. 15(A). Parametric analysis of the E-Field in a transept line is shown through the volume of modified conductivity compared to a baseline profile without CNTs, see FIG. 15(B). The current input was varied to determine the requisite current to produce cortical activation at the boundary of the diffused CNT-Ms. A linear relationship was observed between the applied current and E-field. A current of 32 mA was required to activate the volume of increased conductivity. The expanded surface area provided by the volume of conductive CNT-Ms diminished the charge density to 1.63 $\mu C/phase*cm^{-2}$ when applying 5.12 μC/phase, which is below the damaging threshold, see FIG. 15(C).

Example 10—Conclusions

Human astrocyte viability testing determined that 90% pure raw (unfunctionalized) metallic-type CNTs reduced viability relative to 99% pure metallic-type CNTs at 25 ng/mL. No statistically significant difference in HA viabilities was observed once the CNTs were functionalized. Functionalized CNT-Ms are biocompatible within the brain and can actually modify the biophysical properties of neural cells. CNT-M's change the local conductivity of gel brain phantoms and can enhance the theoretical extent of cortical activation by a depth lead for direct neurostimulation therapy. This study demonstrates a proof-of-concept of potentially building biocompatible carbon-based charge-focusing nanodevices (U.S. Pat. No. 8,788,033) for augmenting neuromodulation at the cellular level. Example of suitable nanodevices are disclosed in U.S. Pat. No. 8,788,033, entitled "Energy-releasing carbon nanotube transponder and method of using same", the contents of which are incorporated by reference.

REFERENCES

1. Rossi M A, et al (2010). Predicting white matter targets for direct neurostimulation therapy. Epilepsy Res 91:176-186.
2. Cendejas-Zaragoza L et al (2014). Development of a depth electrode placement system for direct cortical stimulation. No. 1.074. AES abstract.
3. Cendejas-Zaragoza, L et al (2015). Novel depth electrode placement planning system for direct cortical stimulation therapy and validation using subtracted activated SPECT. No. 2.084. AES Abstract.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

We claim:

1. A method for treating an epileptic seizure in a patient's brain, the method comprising:
    acquiring an inter-ictal imaging profile from the brain of the patient;
    acquiring a post-ictal imaging profile from the brain of the patient;
    comparing the inter-ictal imaging profile and the post-ictal imaging profile by computing fractional anisotropy in the inter-ictal imaging profile and the post-ictal imaging profile and subtracting results of the computing;
    determining an ictal propagation pathway based on the comparing;
    determining a plurality of virtual electrode placement positions for an electrode based on the ictal propagation pathway;
    determining a volume of cortical activation at each of a plurality of virtual electrode placement positions, wherein the volume of cortical activation at a virtual electrode placement position is based on the ictal propagation pathway and the virtual electrode placement position;
    determining a second directional derivative of an electrical potential in a direction of white matter tracts, wherein directionality of the second directional derivative is obtained from tensor fitting acquired from post-ictal diffusion tensor imaging;
    selecting an implantation position for the electrode from the plurality of virtual electrode placement positions, wherein the selecting is based on the volume of cortical activation at the implantation position and the second directional derivative of the electrical potential;
    implanting the electrode or having the electrode implanted at the implantation position; and
    delivering an electrical pulse from the electrode to cellular tissue within the volume of cortical activation, wherein the electrical pulse is of a magnitude effective to at least reduce the epileptic seizure.

2. The method of claim 1, further comprising:
    delivering a plurality of energy-releasing carbon nanotube transponders to a region of the brain of the patient, and
    releasing an electric charge from the plurality of energy-releasing carbon nanotube transponders,
    wherein the energy-releasing carbon nanotube transponders are delivered to the cellular tissue at a position dependent upon ictal propagation pathway.

3. The method of claim 1, wherein acquiring an inter-ictal imaging profile comprises acquiring an inter-ictal diffusion tensor imaging MRI dataset and wherein acquiring a post-ictal imaging profile comprises acquiring a post-ictal diffusion tensor imaging MRI dataset.

4. The method of claim 3, wherein determining the ictal propagation pathway comprises determining the fractional anisotropy in the inter-ictal diffusion tensor imaging MRI dataset and the post-ictal diffusion tensor imaging MRI dataset.

5. The method of claim 1, wherein acquiring an inter-ictal imaging profile further comprises acquiring an inter-ictal single-photon emission computed tomography dataset and wherein acquiring a post-ictal imaging profile further comprises acquiring a post-ictal single-photon emission computed tomography dataset.

6. The method of claim 3, wherein determining the volume of cortical activation at each of a plurality of virtual electrode placement positions comprises determining an activation function, wherein determining the activation function comprises determining the electric potential produced by stimulation of the electrode in a homogeneous medium.

7. The method of claim 3, wherein determining the volume of cortical activation at each of a plurality of virtual electrode placement positions comprises determining an activation function, wherein determining the activation function comprises determining an electric potential produced by stimulation of the electrode in an anisotropic medium.

8. The method of claim 6, comprising determining the direction of white matter tracts from the post-ictal diffusion tensor imaging MRI dataset.

9. The method of claim 1, further comprising:
    acquiring a stimulation activated single-photon emission computed tomography dataset after delivery of the electrical pulse from the electrode;
    comparing the stimulation activated single-photon emission computed tomography dataset with the volume of cortical activation at the implantation position; and
    validating the volume of cortical activation at the implantation position based on the comparing.

10. The method of claim 2, wherein each energy-releasing carbon nanotube transponder comprises:
    (a) at least one carbon nanotube; and
    (b) a nanocapacitor connecting to a first end of the at least one carbon nanotube, wherein the nanocapacitor is capable of storing a predetermined amount of electric energy and releasing the electrical energy in the form of a mean charge density in the range of between about $1.2 \times 10^{-5}$ and about $2.4 \times 10^{-5}$ Coulombs/cm$^2$, and the at least one carbon nanotube connecting to the nanocapacitor and acting as a nanoswitch for releasing the predetermined amount of electrical energy to the cellular tissue in response to a change in the environment of the nanotube transponder, and wherein a plurality of the nanotube transponders is capable of releasing a biologically non-destructive electric charge in the range of between about 4 and about 20 microCoulombs/cm$^2$ to the cellular tissue.

11. The method of claim 2, wherein the plurality of energy-releasing carbon nanotube transponders increases the volume of cortical activation at the implantation position beyond the volume of cortical activation of the electrode.

12. The method of claim 2, wherein the plurality of energy-releasing carbon nanotube transponders is injected into grey and white matter of the brain using a catheter housed within the electrode or by an independent syringe system, and wherein the plurality of energy-releasing carbon nanotube transponders is guided through brain tissue to a critical mode of the brain by an electrical field generated by the electrode.

13. The method of claim 10, further comprising a coiled nanowire located inside the nanocapacitor.

14. The method of claim 10, further comprising a coiled nanowire located outside the nanocapacitor.

15. The method of claim 10, further comprising a biocompatible coating on the outer surface of the energy-releasing carbon nanotube transponder.

16. The method of claim 15, wherein the biocompatible coating is a material selected from the group consisting of polylactic acid (PLA), polyglycolic acid (PGA), poly lactide co-glycolide (PLGA) and chitosan.

17. The method of claim 10, further comprising a molecular label linked to a free end of at least one carbon nanotube, the free end of the carbon nanotube being distal from the nanocapacitor.

18. The method of claim 11, wherein the volume of cortical activation of the electrode extends to at least 4 mm.

19. The method of claim 10, wherein the plurality of energy-releasing carbon nanotube transponders is guided through brain tissue to a critical mode of the brain by an electrical field generated by the electrode.

20. A method for treating a tumor in a patient's brain, the method comprising:
  acquiring baseline diffusion tensor imaging MRI dataset from the brain of the patient;
  determining a tumor position based on the diffusion tensor imaging MRI dataset;
  determining a plurality of virtual electrode placement positions for an electrode based on the tumor position;
  determining a volume of cortical activation at each of a plurality of virtual electrode placement positions, wherein the volume of cortical activation at a virtual electrode placement position is based on the tumor position and the virtual electrode placement position;
  determining a second directional derivative of an electrical potential in a direction of white matter tracts, wherein directionality of the second directional derivative is obtained from tensor fitting acquired from post-ictal diffusion tensor imaging;
  selecting an implantation position for the electrode from the plurality of virtual electrode placement positions, wherein the selecting is based on the volume of cortical activation at the implantation position and the second directional derivative of the electrical potential;
  implanting the electrode at the implantation position; and
  delivering an electrical pulse from the electrode to tumor tissue within the volume of cortical activation, wherein the electrical pulse is of a magnitude to effectively treat the tumor tissue.

21. The method of claim 20, further comprising:
  delivering a plurality of energy-releasing carbon nanotube transponders to a region of the brain of the patient, and
  releasing an electric change from the plurality of energy-releasing carbon nanotube transponders,
  wherein the electric change from the plurality of energy-releasing carbon nanotube transponders pulse is of a magnitude to effectively treat the tumor tissue.

* * * * *